(12) United States Patent
Li et al.

(10) Patent No.: US 9,382,273 B2
(45) Date of Patent: *Jul. 5, 2016

(54) SYNTHESIS OF FOUR COORDINATED PALLADIUM COMPLEXES AND THEIR APPLICATIONS IN LIGHT EMITTING DEVICES THEREOF

(71) Applicant: Arizona Board of Regents Acting for and on Behalf of Arizona State University, Scottsdale, AZ (US)

(72) Inventors: Jian Li, Phoenix, AZ (US); Eric Turner, Phoenix, AZ (US)

(73) Assignee: ARIZONA BOARD OF REGENTS ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/145,461

(22) Filed: Dec. 31, 2013

(65) Prior Publication Data

US 2014/0114072 A1    Apr. 24, 2014

Related U.S. Application Data

(63) Continuation of application No. 13/695,337, filed as application No. PCT/US2011/034776 on May 2, 2011, now abandoned.

(60) Provisional application No. 61/329,684, filed on Apr. 30, 2010.

(51) Int. Cl.
*H01L 51/00* (2006.01)
*C07F 7/24* (2006.01)
(Continued)

(52) U.S. Cl.
CPC .............. *C07F 7/24* (2013.01); *C07D 213/643* (2013.01); *C07F 15/006* (2013.01); *C09K 11/06* (2013.01); *H01L 51/0084* (2013.01); *H05B 33/14* (2013.01); *C09K 2211/1029* (2013.01);
(Continued)

(58) Field of Classification Search
CPC ............ H01L 51/0084; H01L 51/5016; H01L 51/424; Y02E 10/549; C07D 213/643; C07F 15/006; C07F 7/24; C09K 2211/185; C09K 2211/1029; C09K 2211/1044; H05B 33/14
USPC .......................................................... 546/4
See application file for complete search history.

(56) References Cited

U.S. PATENT DOCUMENTS

| | | |
|---|---|---|
| 6,780,528 B2 | 8/2004 | Tsuboyama et al. |
| 7,002,013 B1 | 2/2006 | Chi et al. |

(Continued)

FOREIGN PATENT DOCUMENTS

| | | |
|---|---|---|
| CN | 1777663 A | 5/2006 |
| CN | 1894269 A | 1/2007 |

(Continued)

OTHER PUBLICATIONS

Wong; Journal of Organometallic Chemistry, 2009, 694, 2644-2647.*
JP2009267244, English Translation from EPO, Nov. 2009.*
JP2010135689, English translation from EPO, Jun. 2010.*
Murakami; JP 2007258550, English machine translation from EPO.*
Murakami; JP 2007324309, English machine translation from EPO.*
Chi; Chemical Society Reviews, 2010, 39, 638-655.

(Continued)

*Primary Examiner* — Andrew D Kosar
*Assistant Examiner* — Daniel Carcanague
(74) *Attorney, Agent, or Firm* — Fish & Richardson P.C.

(57) ABSTRACT

Synthesis of four coordinated palladium complexes and their applications in light emitting devices thereof.

13 Claims, 6 Drawing Sheets

(51) Int. Cl.
  C07D 213/643  (2006.01)
  C07F 15/00    (2006.01)
  C09K 11/06    (2006.01)
  H05B 33/14    (2006.01)
  H01L 51/42    (2006.01)
  H01L 51/50    (2006.01)

(52) U.S. Cl.
  CPC ... *C09K2211/1044* (2013.01); *C09K 2211/185* (2013.01); *H01L 51/424* (2013.01); *H01L 51/5016* (2013.01); *Y02E 10/549* (2013.01)

(56) References Cited

U.S. PATENT DOCUMENTS

| | | | |
|---|---|---|---|
| 7,442,797 B2 * | 10/2008 | Itoh et al. | 546/6 |
| 7,501,190 B2 | 3/2009 | Ise | |
| 7,655,322 B2 | 2/2010 | Forrest et al. | |
| 7,947,383 B2 | 5/2011 | Ise et al. | |
| 8,816,080 B2 | 8/2014 | Li et al. | |
| 8,927,713 B2 | 1/2015 | Li et al. | |
| 8,946,417 B2 | 2/2015 | Jian et al. | |
| 9,059,412 B2 | 6/2015 | Zeng et al. | |
| 9,224,963 B2 | 12/2015 | Li et al. | |
| 9,238,668 B2 | 1/2016 | Li et al. | |
| 2002/0068190 A1 | 6/2002 | Tsuboyama et al. | |
| 2005/0260446 A1 | 11/2005 | Mackenzie et al. | |
| 2006/0073359 A1 | 4/2006 | Ise et al. | |
| 2006/0202197 A1 | 9/2006 | Nakayama et al. | |
| 2006/0210831 A1 | 9/2006 | Sano et al. | |
| 2006/0263635 A1 | 11/2006 | Ise | |
| 2006/0286406 A1 | 12/2006 | Igarashi et al. | |
| 2007/0057630 A1 | 3/2007 | Nishita et al. | |
| 2007/0059551 A1 | 3/2007 | Yamazaki | |
| 2007/0082284 A1 | 4/2007 | Stoessel et al. | |
| 2007/0103060 A1 | 5/2007 | Itoh et al. | |
| 2008/0001530 A1 | 1/2008 | Ise et al. | |
| 2008/0036373 A1 | 2/2008 | Itoh et al. | |
| 2008/0054799 A1 | 3/2008 | Satou | |
| 2008/0079358 A1 | 4/2008 | Satou | |
| 2008/0241518 A1 | 10/2008 | Satou et al. | |
| 2008/0241589 A1 | 10/2008 | Fukunaga et al. | |
| 2009/0026936 A1 | 1/2009 | Satou et al. | |
| 2009/0026939 A1 | 1/2009 | Kinoshita et al. | |
| 2009/0032989 A1 | 2/2009 | Karim et al. | |
| 2009/0039768 A1 | 2/2009 | Igarashi et al. | |
| 2009/0079340 A1 | 3/2009 | Kinoshita et al. | |
| 2009/0128008 A1 | 5/2009 | Ise et al. | |
| 2009/0218561 A1 | 9/2009 | Kitamura et al. | |
| 2009/0261721 A1 | 10/2009 | Murakami et al. | |
| 2009/0267500 A1 | 10/2009 | Kinoshita et al. | |
| 2010/0000606 A1 | 1/2010 | Thompson et al. | |
| 2010/0013386 A1 | 1/2010 | Thompson et al. | |
| 2010/0171111 A1 | 7/2010 | Takada et al. | |
| 2012/0095232 A1 * | 4/2012 | Li et al. | 546/4 |
| 2012/0181528 A1 | 7/2012 | Takada et al. | |
| 2012/0215001 A1 | 8/2012 | Li et al. | |
| 2012/0302753 A1 | 11/2012 | Li | |
| 2013/0048963 A1 | 2/2013 | Beers et al. | |
| 2013/0168656 A1 | 7/2013 | Tsai et al. | |
| 2013/0203996 A1 | 8/2013 | Li et al. | |
| 2013/0237706 A1 * | 9/2013 | Li et al. | 546/4 |
| 2013/0341600 A1 | 12/2013 | Lin et al. | |
| 2014/0014922 A1 | 1/2014 | Lin et al. | |
| 2014/0027733 A1 | 1/2014 | Zeng et al. | |
| 2014/0084261 A1 | 3/2014 | Brooks et al. | |
| 2014/0330019 A1 | 11/2014 | Li et al. | |
| 2014/0364605 A1 | 12/2014 | Li et al. | |
| 2015/0008419 A1 | 1/2015 | Li et al. | |
| 2015/0069334 A1 | 3/2015 | Xia et al. | |
| 2015/0162552 A1 | 6/2015 | Li et al. | |
| 2015/0228914 A1 | 8/2015 | Li et al. | |
| 2015/0287938 A1 | 10/2015 | Li et al. | |
| 2015/0318500 A1 | 11/2015 | Li | |
| 2015/0349279 A1 | 12/2015 | Li et al. | |
| 2016/0028028 A1 | 1/2016 | Li et al. | |
| 2016/0043331 A1 | 2/2016 | Li et al. | |

FOREIGN PATENT DOCUMENTS

| | | |
|---|---|---|
| CN | 101142223 A | 3/2008 |
| CN | 101667626 A | 3/2010 |
| CN | 102449108 A | 5/2012 |
| CN | 102892860 A | 1/2013 |
| CN | 102971396 A | 3/2013 |
| CN | 104232076 A | 12/2014 |
| CN | 104693243 A | 6/2015 |
| EP | 1808052 | 7/2007 |
| EP | 1874893 | 1/2008 |
| EP | 1874894 | 1/2008 |
| EP | 1919928 | 5/2008 |
| EP | 2096690 A2 | 9/2009 |
| EP | 2036907 B1 | 2/2012 |
| EP | 2417217 | 2/2012 |
| EP | 2112213 | 7/2012 |
| EP | 2711999 A2 | 3/2014 |
| JP | 2005267557 A | 9/2005 |
| JP | 2005310733 A | 11/2005 |
| JP | 2006047240 A | 2/2006 |
| JP | 2006232784 A | 9/2006 |
| JP | 2006242080 A | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007042875 A | 2/2007 |
| JP | 2007053132 A | 3/2007 |
| JP | 2007066581 A | 3/2007 |
| JP | 2007073620 A | 3/2007 |
| JP | 2007073845 A | 3/2007 |
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 A | 4/2007 |
| JP | 2007096259 A | 4/2007 |
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009266943 A | 11/2009 |
| JP | 2009267171 | 11/2009 |
| JP | 2009267244 * | 11/2009 |
| JP | 2009272339 | 11/2009 |
| JP | 2009283891 | 12/2009 |
| JP | 2010135689 * | 6/2010 |
| JP | 5604505 | 10/2012 |
| JP | 2012222255 | 11/2012 |
| JP | 2013525436 | 6/2013 |
| JP | 5604505 | 10/2014 |
| JP | 2014221807 | 11/2014 |
| JP | 2015081257 A | 4/2015 |
| KR | 1020060115371 | 11/2006 |
| KR | 2007061830 | 6/2007 |

(56) References Cited

FOREIGN PATENT DOCUMENTS

| KR | 2007112465 | | 11/2007 |
|---|---|---|---|
| KR | 1020130043460 | | 4/2013 |
| TW | 200701835 | | 1/2007 |
| TW | 201307365 | | 2/2013 |
| WO | WO-00/70655 | A2 | 11/2000 |
| WO | WO-2004/108857 | A1 | 12/2004 |
| WO | WO-2005/042444 | A2 | 5/2005 |
| WO | WO-2005/042550 | A1 | 5/2005 |
| WO | WO2006033440 | | 3/2006 |
| WO | WO2008066192 | | 6/2006 |
| WO | WO2006098505 | | 9/2006 |
| WO | WO2006115299 | | 11/2006 |
| WO | WO2006115301 | | 11/2006 |
| WO | WO 2007/034985 | * | 3/2007 |
| WO | WO-2007/069498 | A1 | 6/2007 |
| WO | WO2008066195 | | 6/2008 |
| WO | WO2008066196 | | 6/2008 |
| WO | WO2008117889 | | 10/2008 |
| WO | WO2008123540 | A2 | 10/2008 |
| WO | WO2009017211 | | 2/2009 |
| WO | WO 2010118026 | * | 10/2010 |
| WO | WO2011137429 | | 11/2011 |
| WO | WO2011137431 | | 11/2011 |
| WO | WO2012112853 | | 8/2012 |
| WO | WO2012142387 | A1 | 10/2012 |
| WO | WO2012162488 | | 11/2012 |
| WO | WO2012163471 | | 12/2012 |
| WO | WO2013130483 | | 9/2013 |
| WO | WO2014031977 | | 2/2014 |
| WO | WO2014047616 | | 3/2014 |
| WO | WO2014109814 | | 7/2014 |
| WO | WO2016025921 | A1 | 2/2016 |
| WO | WO2016029186 | A1 | 2/2016 |

OTHER PUBLICATIONS

Dorwald; Side Reactions in Organic Synthesis: A Guide to Successful Synthesis Design, 2005, Wiley-VCH.
Satake; Organometallics, 1999, 18, 5108-5111.
Non-Final Rejection issued on Jul. 1, 2013 for U.S. Appl. No. 13/695,337, filed May 2, 2011 (Applicants—Arizona Technology Enterprises (AZTE); Inventors—Li et al.; (28 pages).
Preliminary Amendment filed on Oct. 30, 2012 for U.S. Appl. No. 13/695,337, filed May 2, 2011 (Applicants—Arizona Technology Enterprises (AZTE); Inventors—Li et al.; (4 pages).
International Preliminary Report on Patentability issued on Nov. 6, 2012 for Intl. Pat. App. No. PCT/US2011/034776 filed May 2, 2011 and published as WO 2011/137429 on Nov. 3, 2011 (Applicants—Arizona Board of Regents Acting for and on behalf of Arizona State University; Inventors—Li et al.; (6 pages).
International Search Report mailed on Feb. 9, 2012 for Intl. Pat. App. No. PCT/US2011/034776 filed May 2, 2011 and published as WO 2011/137429 on Nov. 3, 2011 (Applicants—Arizona Board of Regents Acting for and on behalf of Arizona State University; Inventors—Li et al.; (3 pages).
Written Opinion mailed on Feb. 9, 2012 for Intl. Pat. App. No. PCT/US2011/034776 filed May 2, 2011 and published as WO 2011/137429 on Nov. 3, 2011 (Applicants—Arizona Board of Regents Acting for and on behalf of Arizona State University; Inventors—Li et al.; (5 pages).
Baldo et al., "Highly Efficient Phosphorescent Emission from Organic Electroluminescent Devices," Nature, vol. 395, 151-154, 1998.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6 Aug. 25, 2013.
First Office Action (and English Translation) for Chinese Application No. 201180023966.1, issued Feb. 7, 2014, 14 pages.
Baldo et al., "Very high-efficiency green organic light-emitting devices based on electrophosphorescence," Applied Physics Letters, vol. 75, No. 1, Jul. 5, 1999, pp. 4-6.
Second Office Action (and English Translation) for Chinese Application No. 201180023966.1, issued Dec. 22, 2014, 8 pages.
International Search Report and Written Opinion mailed by the International Searching Authority on May 14, 2015 for PCT/US2015/018195 filed Feb. 27, 2015, 17 pages.
Ayan Maity et al., "Room-temperature synthesis of cyclometalated iridium(III) complexes; kinetic isomers and reactive functionalities", Chem. Sci., vol. 4, 2013, pp. 1175-1181.
Shiro Koseki et al., "Spin-orbit coupling analyses of the geometrical effects on phosphorescence in Ir(ppy)3 and its derivatives", J. Phys. Chem. C, vol. 117, 2013, pp. 5314-5327.
Ji Hyun Seo et al., "Efficient blue-green organic light-emitting diodes based on heteroleptic tris-cyclometalated iridium (III) complexes", Thin Solid Films, vol. 517, 2009, pp. 1807-1810.
Official Action (and English Translation) issued by the Japanese Patent Office on Mar. 11, 2015 for Pat. App. No. 2013-508082 filed May 2, 2011, 16 pages.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Indium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater, vol. 16, 2004, pp. 4743-4747.
Dorwald; "Side Reactions in Organic Synthesis: A Guide to Successful Synthesis Design," Chapter 1, 2005 Wiley-VCH Verlag GmbH & Co. KGaA, Wienheim.
Third Office Action (and English Translation) for Chinese Application No. 201180023966.1, issued Sep. 1, 2015, 7 pages.
Final Rejection (and English Translation) issued by the Japanese Patent Office on Oct. 30, 2015 for Pat. App. No. 2013-508082, 6 pages.

* cited by examiner (A)

(B)

(A)

(B)

(C)

(D)

SYNTHESIS OF FOUR COORDINATED PALLADIUM COMPLEXES AND THEIR APPLICATIONS IN LIGHT EMITTING DEVICES THEREOF

CROSS-REFERENCE TO RELATED APPLICATIONS

The present application is a Continuation of U.S. patent application Ser. No. 13/695,337, filed Mar. 13, 2013, which claims priority to and is a U.S. National Phase Application of International Application No. PCT/US2011/034776, filed May 2, 2011, which claims priority to U.S. Patent Application No. 61/329,684, filed Apr. 30, 2010, all of which applications are incorporated herein fully by this reference.

BACKGROUND

1. Technical Field

The present disclosure relates to palladium complexes which are capable of absorbing and/or emitting light and are thus useful as an emissive or absorption material in a device.

2. Technical Background

Compounds capable of absorbing and/or emitting light are ideally suited for use in a wide variety of optical and electro-optical devices, including photo-absorbing devices such as solar and photo-sensitive devices, photo-emitting devices, such as organic light emitting diodes (OLEDs), or devices capable of both photo-absorption and emission. Much research has been devoted to the discovery and optimization of organic and organometallic materials for use in optical and electro-optical devices. Generally, research in this area aims to accomplish a number of goals, including improvements in absorption and emission efficiency, as well as improvements in processing ability, among others.

Despite significant advances in research devoted to optical and electro-optical materials, many current devices comprising organic or organometallic materials have yet to be optimized Many materials currently used in optical and electro-optical devices have a number disadvantages, including poor processing ability, inefficient emission or absorption, and less than ideal stability, among others. Thus, a need exists for new materials which exhibit improved performance in optical and electro-optical devices. This need and other needs are satisfied by the compositions and methods of the present invention.

SUMMARY

The present invention relates to palladium complexes that exhibit photo-absorption and photo-emission, to methods of making such compounds, and to applications thereof, including optical devices comprising the compounds.

In one embodiment, the compounds are represented by the formula:

wherein each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol;

$R^3$ represents methyl, ethyl, propyl, or butyl;

$Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl;

n is an integer 0 or 1;

$Y^{1b}$ when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl;

each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol;

each Of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl;

wherein m is an integer 1 or 2;

wherein the open dotted circle indicates partial or full unsaturation of the ring with which it is associated;

provided that if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$, or $Y^{3d}$ is not N; and provided that if n is 0, m is 2, each of $Y^{2a}$ and $Y^{2d}$ is CH, and each of $Y^{2b}$ and $Y^{2c}$ is N, then at least one of $Y^{3b}$ or $Y^{3c}$ is not N.

Also disclosed are optical devices, such as organic light emitting devices and luminescent display devices that comprise one or more compounds of the invention as a functional material, such as a light-emitter or absorber, or both.

BRIEF DESCRIPTION OF THE FIGURES

The accompanying figures, which are incorporated in and constitute a part of this specification, illustrate several aspects and together with the description serve to explain the principles of the invention.

Figure 1:
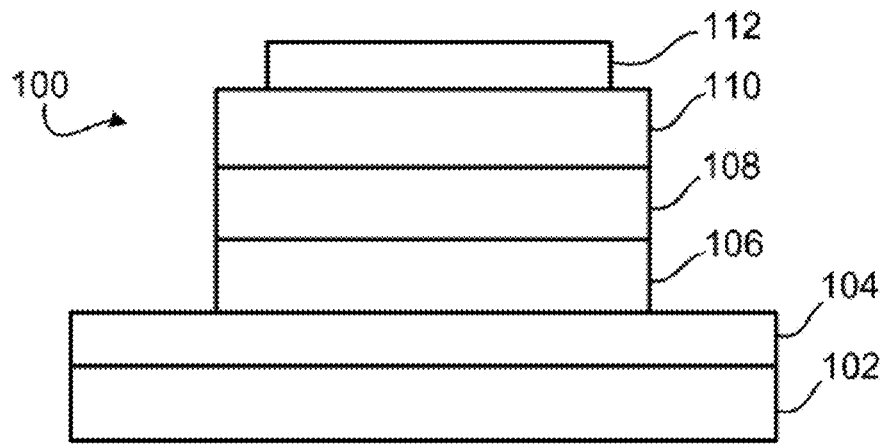
FIG. 1 is a drawing of a cross-section of an exemplary organic light-emitting diode (OLED).
Figure 2:
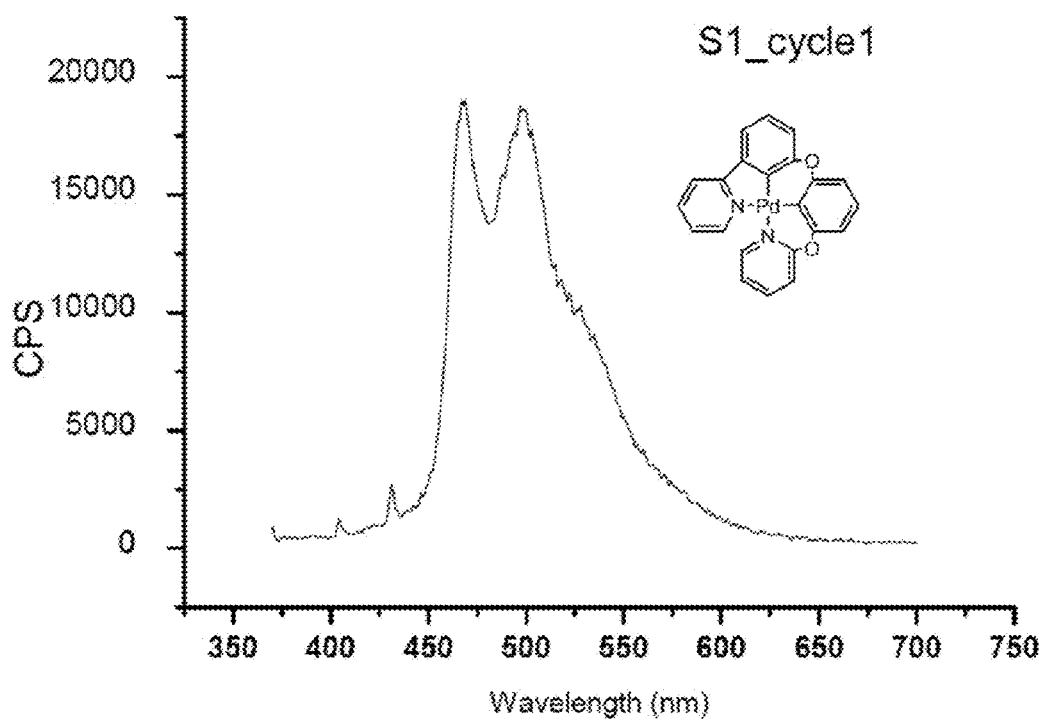
FIG. 2 is a photoluminescence spectrum produced from a specific embodiment, 2-(3-(pyridin-2-yl)phenoxy)-6-(pyridin-2-yloxy)phenyl]Pd(II) (Pd003) taken in degassed dichloromethane at room temperature, wherein the quantum yield was about 0.1 and the luminescence lifetime was about 11 μsec. The chemical structure of Pd003 is also illustrated in the inset.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

Throughout the specification, it should be understood that where letters and/or symbols are utilized to represent atoms or functional groups, and wherein multiple instances of the same letter and/or symbol are present, that each individual instance can represent the same or different species (e.g., atom and/or functional group) than any other instance using the same letter and/or symbol. Similarly, when a metal is depicted as a portion of a chemical structure, the notation can refer to a single metal atom and/or to a plurality of atoms. In one aspect, a notation for a metal refers to a single metal atom. In another aspect, a notation for a metal refers to a plurality of metal atoms.

In one aspect, the invention comprises phosphorescent multidentate, for example, tridentate and/or tetradentate, palladium (II) complexes. In another aspect, such multidentate palladium complexes can be modified and/or specifically tailored to tune the emission spectra from, for example, ultraviolet to near-infrared emission. In yet another aspect, the inventive compositions can provide improved stability and efficiency over conventional light emitting materials. In yet other aspects, the inventive compositions can be useful as luminescent labels, absorbers, emitters, or a combination thereof.

In one aspect, the inventive compositions are represented by the general formula:

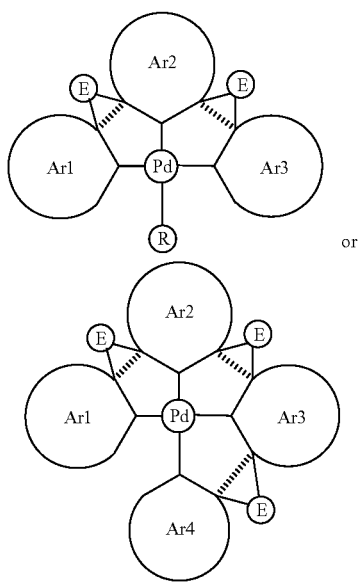

or wherein Ar1, Ar2, Ar3, and Ar4, if present, represent aromatic groups, wherein each E represents an optional linking atom, such as, for example, carbon or oxygen, and wherein R, if present, represents an ancillary ligand In various aspects, an ancillary ligand can comprise one or more of the following:

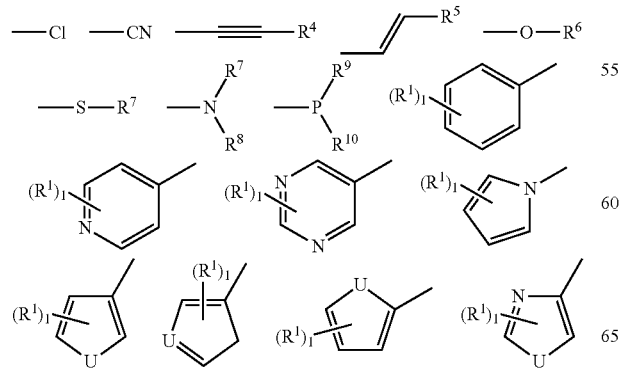

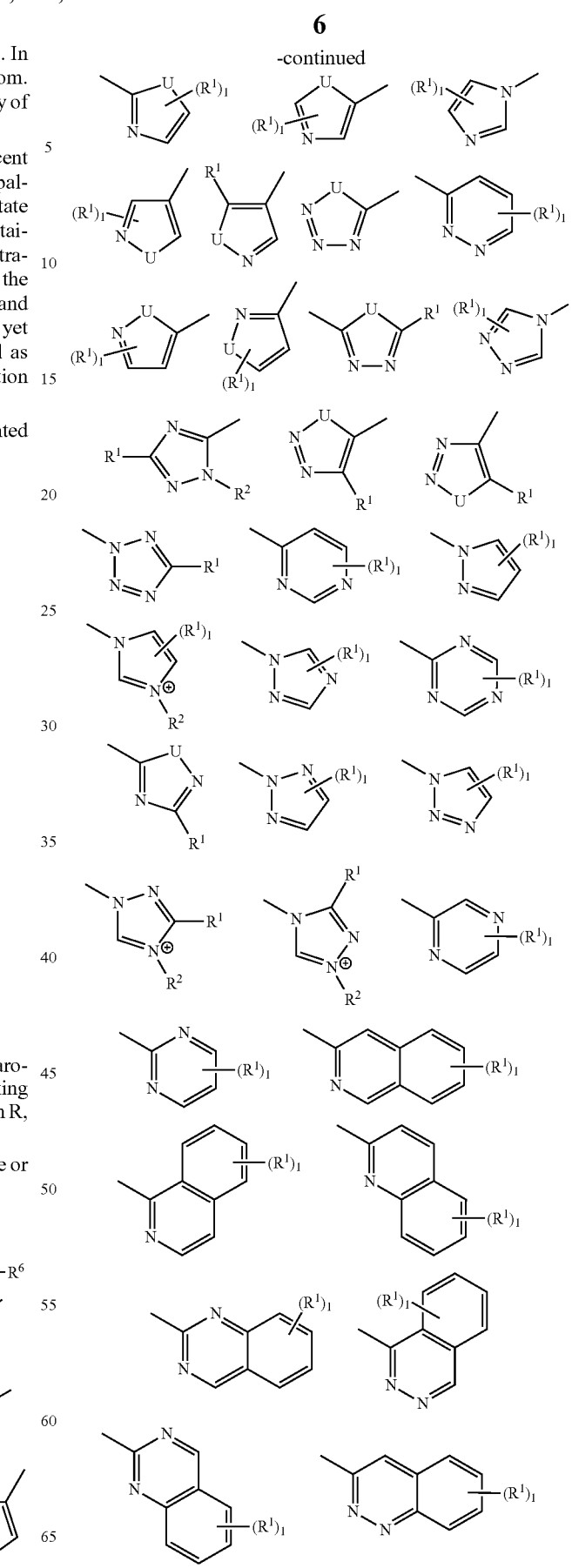

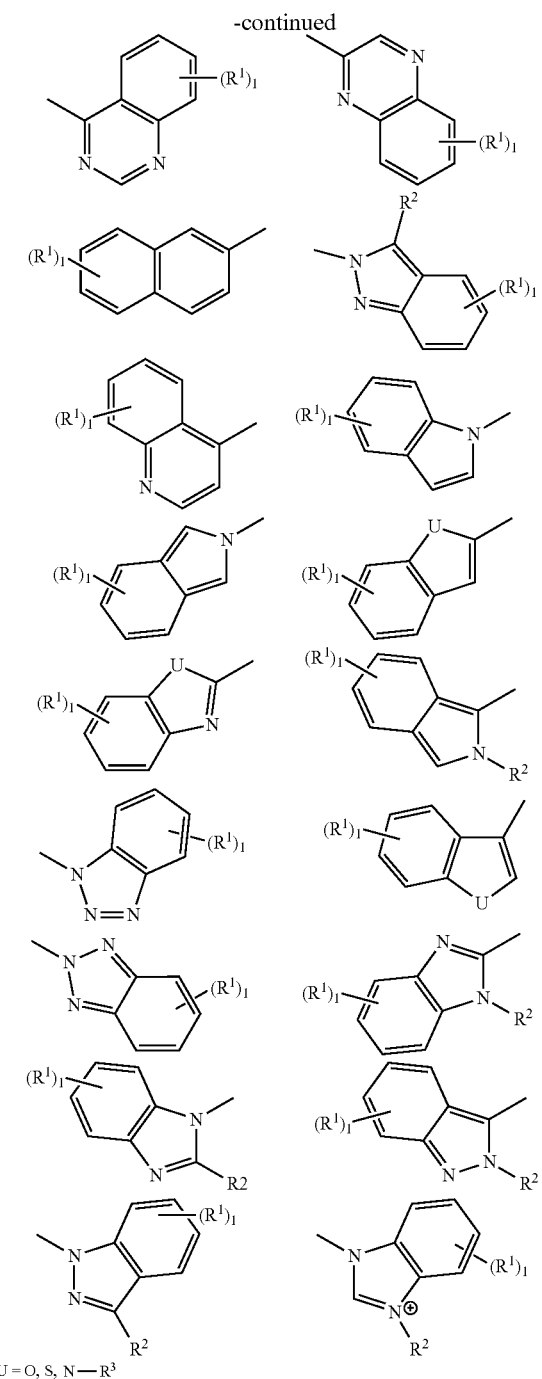

U = O, S, N—R³ wherein, $R^1$-$R^{10}$ of the ancillary ligand each independently represent a hydrogen atom, an alkyl group, a haloalkyl group, an aralkyl group, an alkenyl group, an alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a hydroxyl group, amercapto group, a halogen atom, a cyano group, a sulfo group, a carboxyl group, a nitro group, a hydrzino group, a substituted silyl group, or a polymerizalbe group; further, wherein a plurality of Rs exist, the number of R should be from 0 to about 4, and each R can be the same or different from any other R. In one aspect, an ancillary ligand can comprise a hydrogen atom. In another aspect, an ancillary ligand can comprise an alkyl group. In another aspect, an ancillary ligand can comprise a haloalkyl group. In another aspect, an ancillary ligand can comprise a aralkyl group. In another aspect, an ancillary ligand can comprise a alkenyl group. In another aspect, an ancillary ligand can comprise an alkynl group. In another aspect, an ancillary ligand can comprise an aryl group. In another aspect, an ancillary ligand can comprise an amino group. In another aspect, an ancillary ligand can comprise an alkoxy group, an aryloxy group, a heteroaryloxy group, an alkoxycarbonyl group, an acyloxy group, or a combination thereof. In other aspects, an ancillary ligand can comprise an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a hydroxyl group, amercapto group, a halogen atom, a cyano group, a sulfo group, a carboxyl group, a nitro group, a hydrzino group, a substituted silyl group, a polymerizalbe group, or a combination thereof.

In still other aspects, an ancillary ligand can comprise a group or groups difference from those specifically recited herein, and the present invention is not intended to be limited to any particular ancillary ligand.

In various aspects, specific non-limiting examples of the inventive composition can be grouped and illustrated by ligand class. In one aspect, the inventive composition can be represented by the general formula:

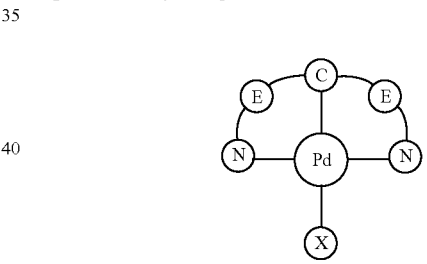

wherein Pd represents palladium, each N represents a nitrogen substituted aromatic group, each E represents an optional linking atom, such as, for example, carbon or oxygen, X represents a halogen or other electronegative group, and C represents an aromatic group. Specific examples of inventive compositions within this ligand class can comprise:

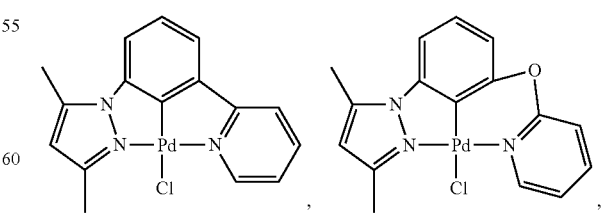

or a combination thereof.

In one aspect, the inventive composition can be represented by the general formula:

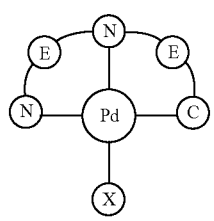

wherein Pd represents palladium, each N represents a nitrogen substituted aromatic group, each E represents an optional linking atom, such as, for example, carbon or oxygen, X represents a halogen or other electronegative group, and C represents an aromatic group. Specific examples of inventive composition within this ligand class can comprise:

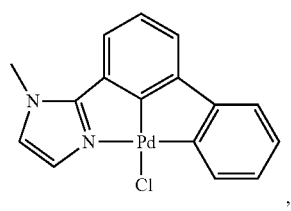

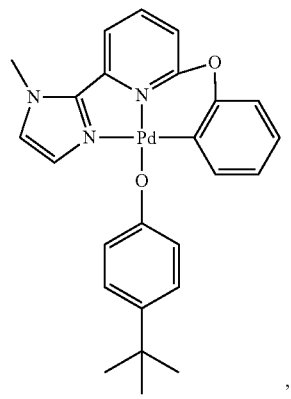

or a combination thereof.

In one aspect, the inventive composition can be represented by the general formula:

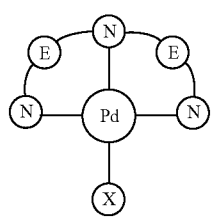

wherein Pd represents palladium, each N represents a nitrogen substituted aromatic group, each E represents an optional linking atom, such as, for example, carbon or oxygen, and X represents a halogen or other electronegative group. Specific examples of inventive composition within this ligand class can comprise:

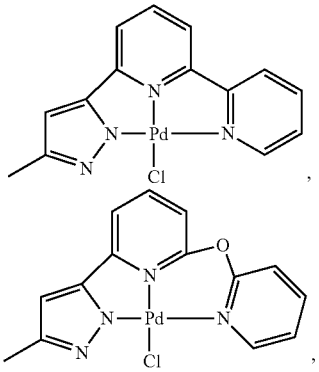

or a combination thereof.

In one aspect, the inventive composition can be represented by the general formula:

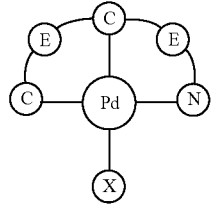

wherein Pd represents palladium, N represents a nitrogen substituted aromatic group, each E represents an optional linking atom, such as, for example, carbon or oxygen, X represents a halogen or other electronegative group, and each C represents an aromatic group. Specific examples of inventive composition within this ligand class can comprise:

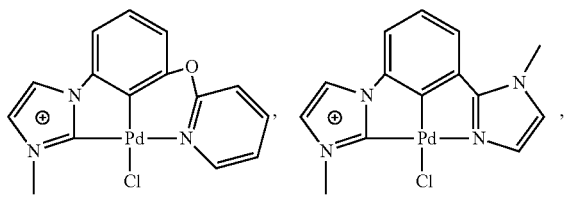

or a combination thereof.

In one aspect, the inventive composition can be represented by the general formula:

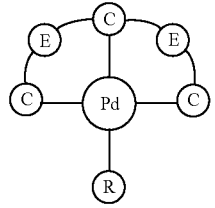

wherein Pd represents palladium, each E represents an optional linking atom, such as, for example, carbon or oxygen, R represents an ancillary ligand, and each C represents an aromatic group. Specific examples of inventive composition within this ligand class can comprise:

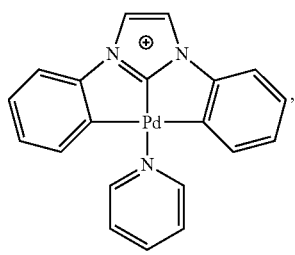

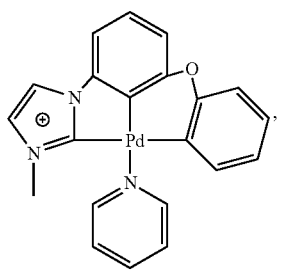

or a combination thereof.

In one aspect, the inventive composition can be represented by the general formula:

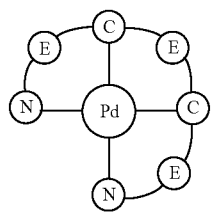

wherein Pd represents palladium, each N represents a nitrogen substituted aromatic group, each E represents an optional linking atom, such as, for example, carbon or oxygen, and each C represents an aromatic group. Specific examples of inventive composition within this ligand class can comprise:

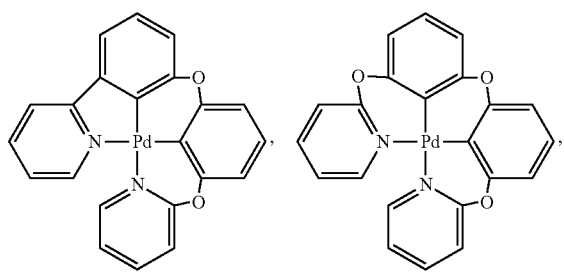

or a combination thereof.

In one aspect, the inventive composition can be represented by the general formula:

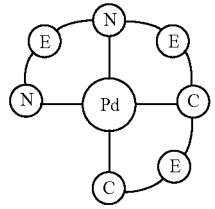

wherein Pd represents palladium, each N represents a nitrogen substituted aromatic group, each E represents an optional linking atom, such as, for example, carbon or oxygen, and each C represents an aromatic group. Specific examples of inventive composition within this ligand class can comprise:

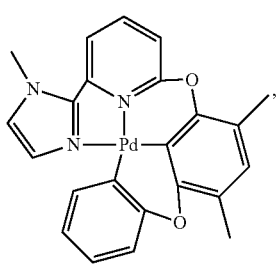

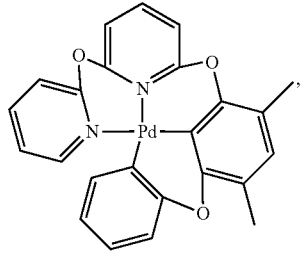

or a combination thereof.

In one aspect, the inventive composition can be represented by the general formula:

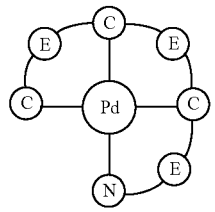

wherein Pd represents palladium, N represents a nitrogen substituted aromatic group, each E represents an optional linking atom, such as, for example, carbon or oxygen, and each C represents an aromatic group. Specific examples of inventive composition within this ligand class can comprise:

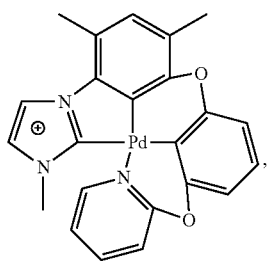

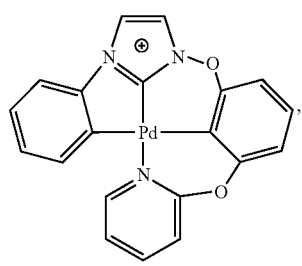

or a combination thereof.

In one aspect, the inventive composition can be represented by the general formula:

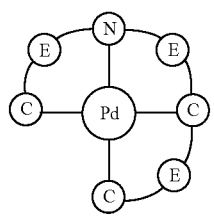

wherein Pd represents palladium, N represents a nitrogen substituted aromatic group, each E represents an optional linking atom, such as, for example, carbon or oxygen, and each C represents an aromatic group. A specific example of an inventive composition within this ligand class can comprise:

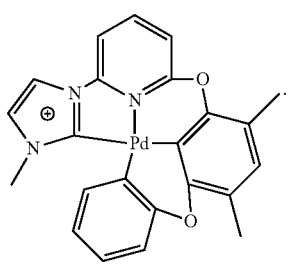

In one aspect, the inventive composition can be represented by the general formula:

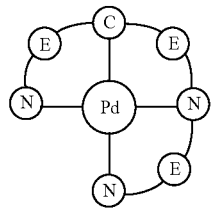

wherein Pd represents palladium, each N represents a nitrogen substituted aromatic group, each E represents an optional linking atom, such as, for example, carbon or oxygen, and C represents an aromatic group. Specific examples of inventive compositions within this ligand class can comprise:

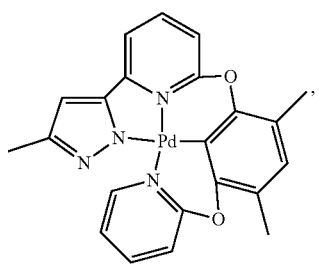

or a combination thereof.

In one aspect, the inventive composition can be represented by the general formula:

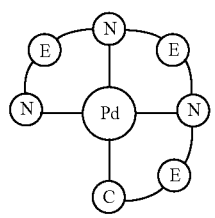

wherein Pd represents palladium, each N represents a nitrogen substituted aromatic group, each E represents an optional linking atom, such as, for example, carbon or oxygen, and C represents an aromatic group. A specific example of an inventive composition within this ligand class can comprise:

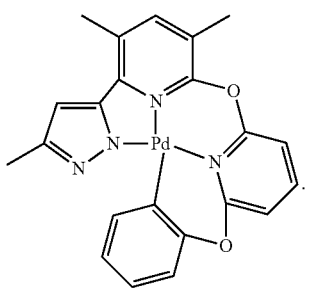

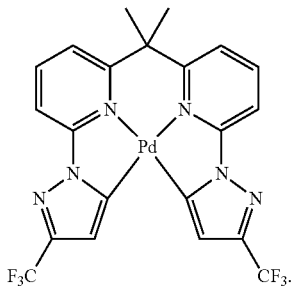

In another aspect, the compounds of the present invention are represented by the formula:

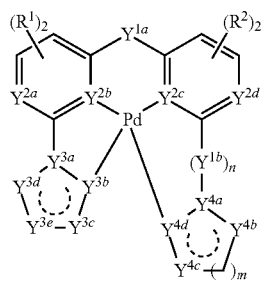

In the above formula, each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol; $Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl; n is an integer 0 or 1; $Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl; each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol; each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl; m is an integer 1 or 2; wherein the open dotted circle $$\stackrel{\cdots}{(\ \ )}$$

indicates partial or full unsaturation of the ring with which it is associated.

In one embodiment of the formula above, if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$ or $Y^{3d}$ is not N. For example, according to this embodiment, the following compound is not included in the above formula:

As can be seen in the preceding example above, m is 1, each of $Y^{2a}$ and $Y^{2d}$ is CH and each of $Y^{2b}$ and $Y^{2c}$ is N; however, each of $Y^{4a}$, $Y^{4b}$, $Y^{3a}$, or $Y^{3d}$ is N. It follows that the preceding example, according to this embodiment, is not included within the general formula above. In the practice of this embodiment, similar analysis can be used to determine whether or not a compound is or is not included within the general formula above.

In a further embodiment of the general formula above, if n is 0, m is 2, each of $Y^{2a}$ and $Y^{2d}$ is CH, and each of $Y^{2b}$ and $Y^{2c}$ is N, then at least one of $Y^{3b}$ or $Y^{3c}$ is not N. For example, according to this embodiment, the following compound is not included in the above formula:

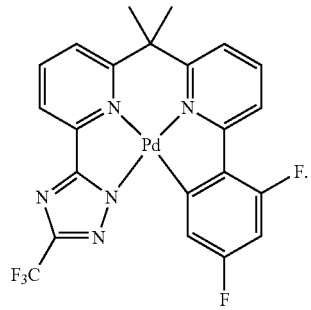

As can be seen in the preceding example above, n is 0, m is 2, each of $Y^{2a}$ and $Y^{2d}$ is CH, and each of $Y^{2b}$ and $Y^{2c}$ is N. However, each of $Y^{3b}$ and $Y^{3c}$ is N. It follows that the preceding example, according to this embodiment, is not included within the general formula above. Once more, in the practice of this embodiment, similar analysis can be used to determine whether or not a compound is or is not included within the general formula above.

In one embodiment of the general formula above, the compound is represented by the formula:

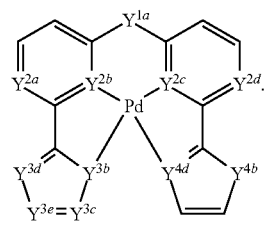

Non-limiting examples of specific embodiments within this formula include:

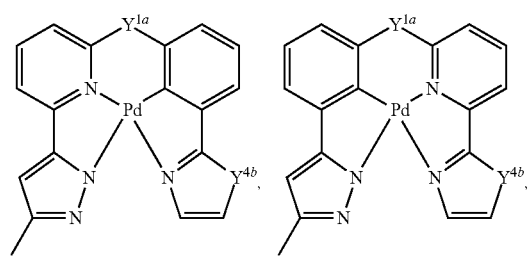
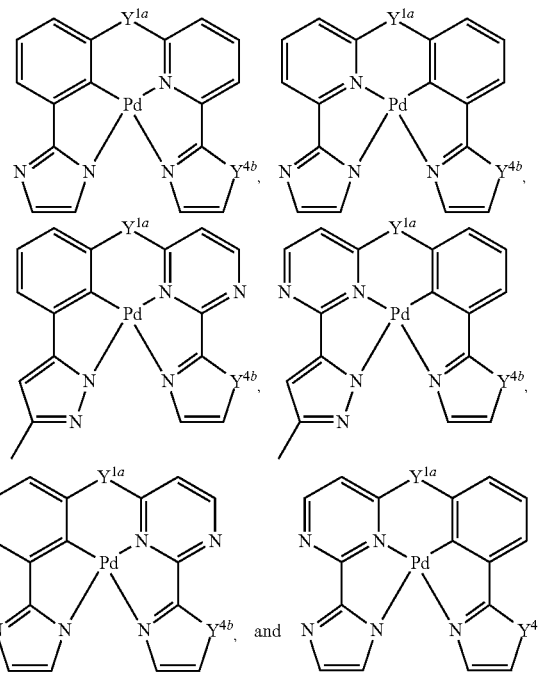
In another embodiment of the general formula above, the compound is represented by the formula:
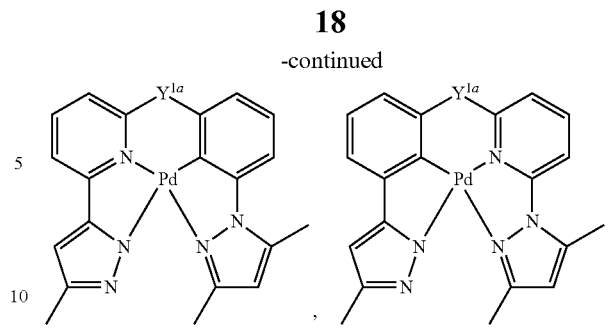
Non-limiting examples of specific embodiments within this formula include:
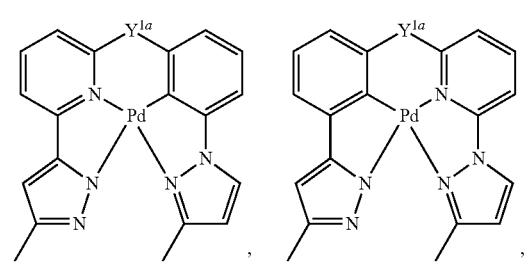
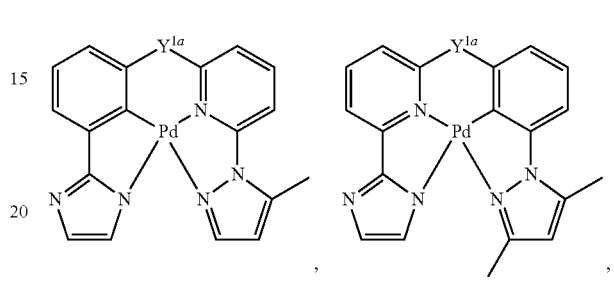
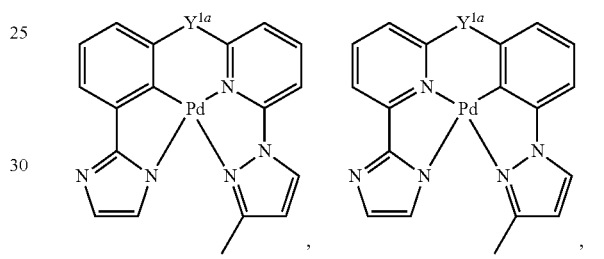
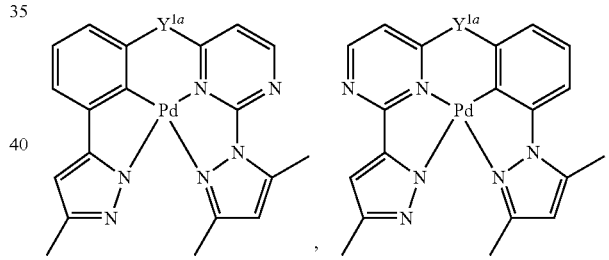
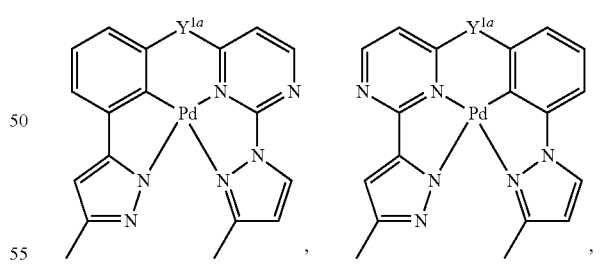

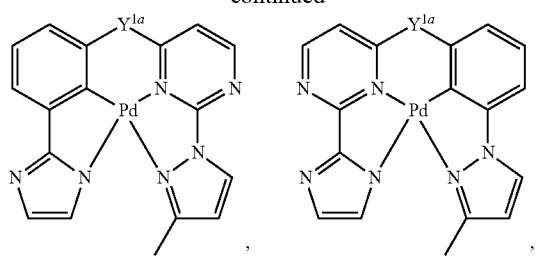
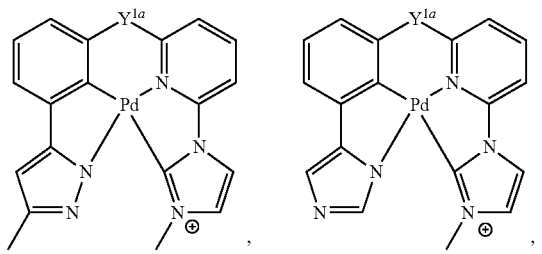
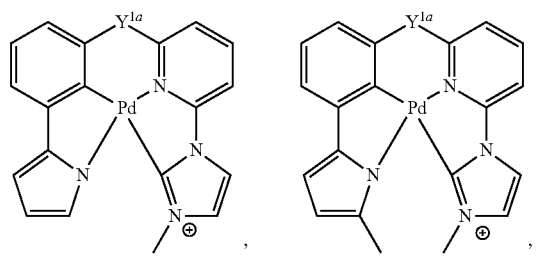
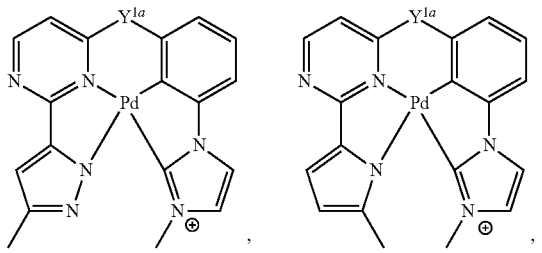
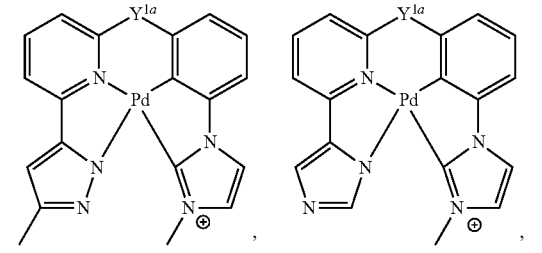
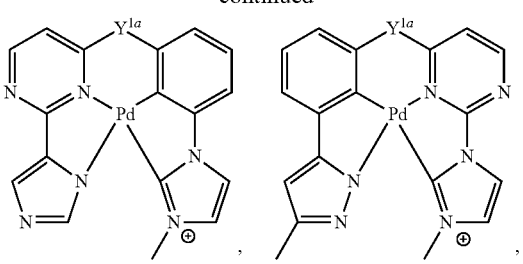
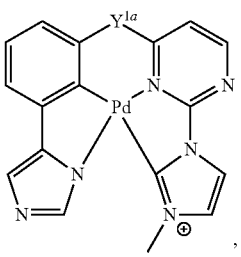
, and
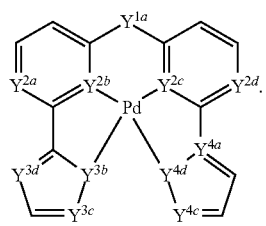
.
In another embodiment of the general formula above, the compound is represented by the formula:
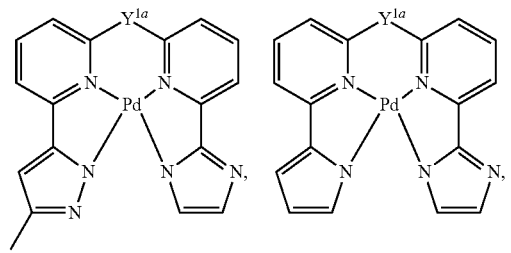
Non-limiting examples of specific embodiments within this formula include:

-continued
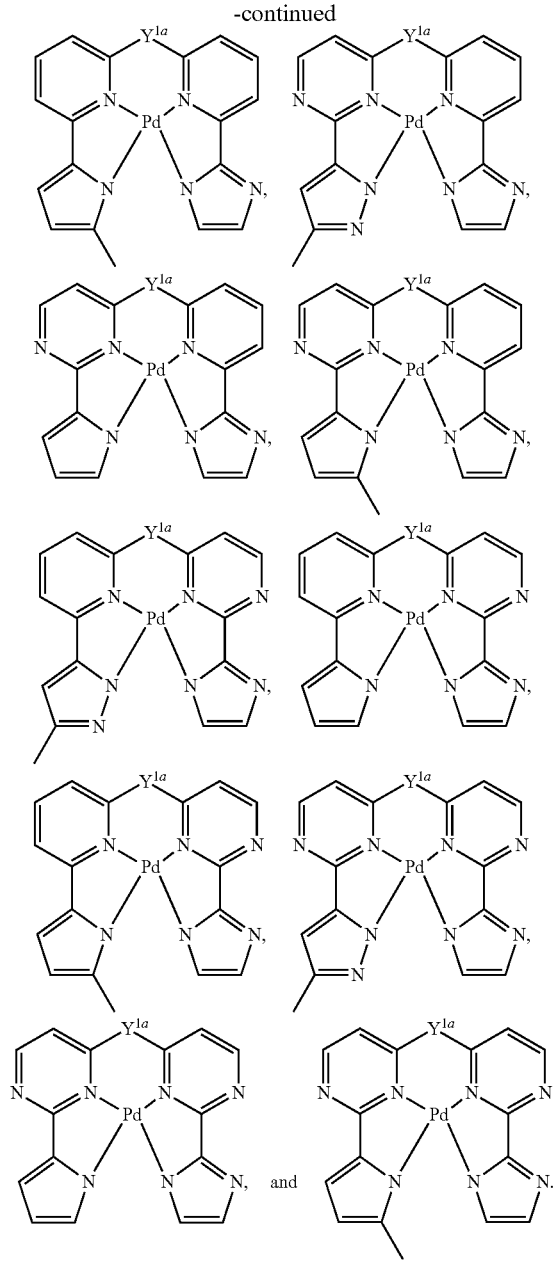
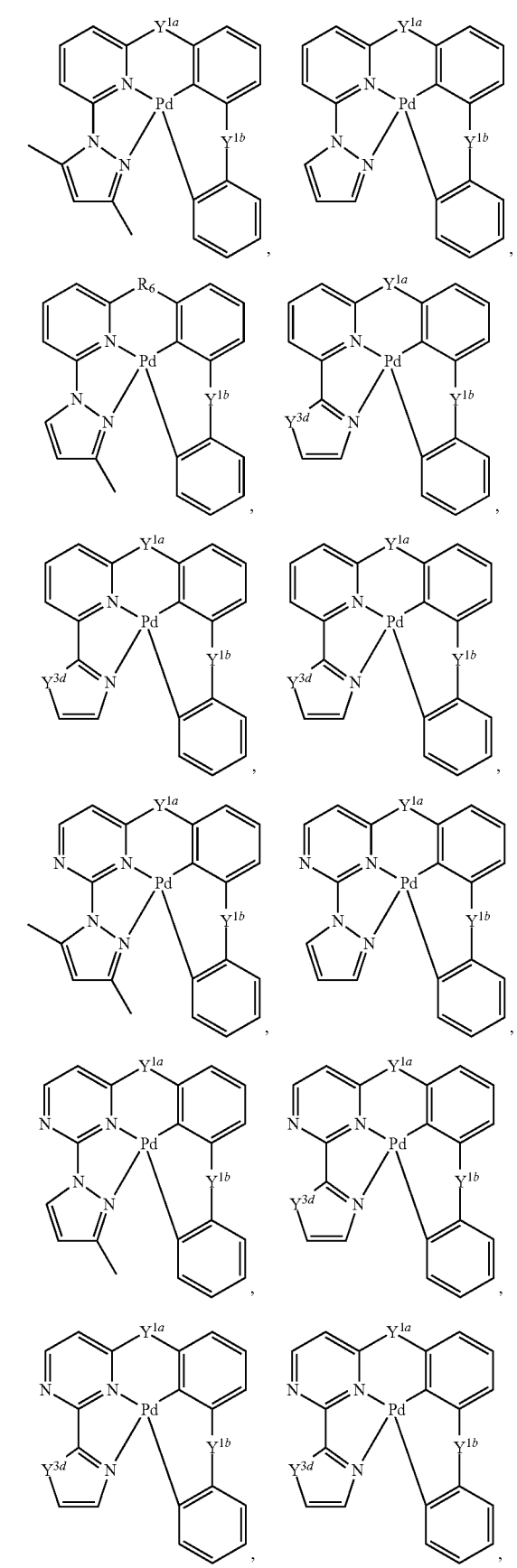
In another embodiment of the general formula above, the compound is represented by the formula:
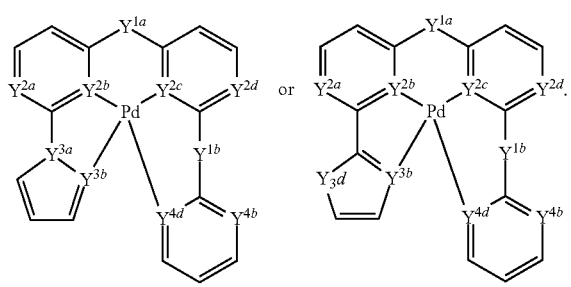
Non-limiting examples of specific embodiments within this formula include:

-continued
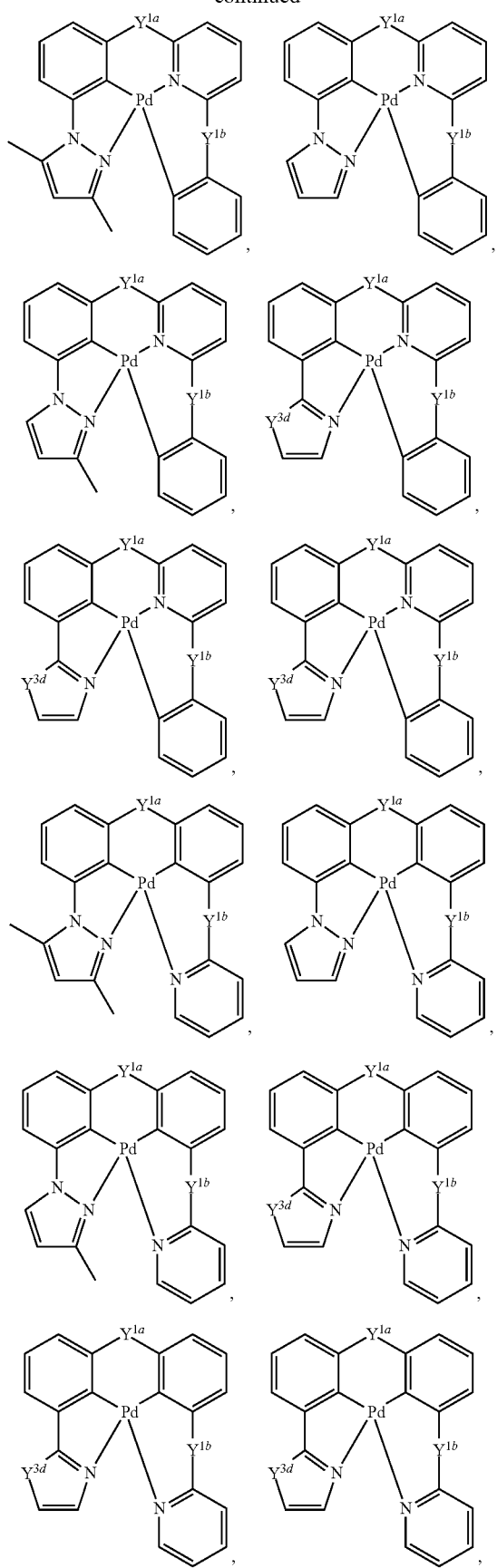
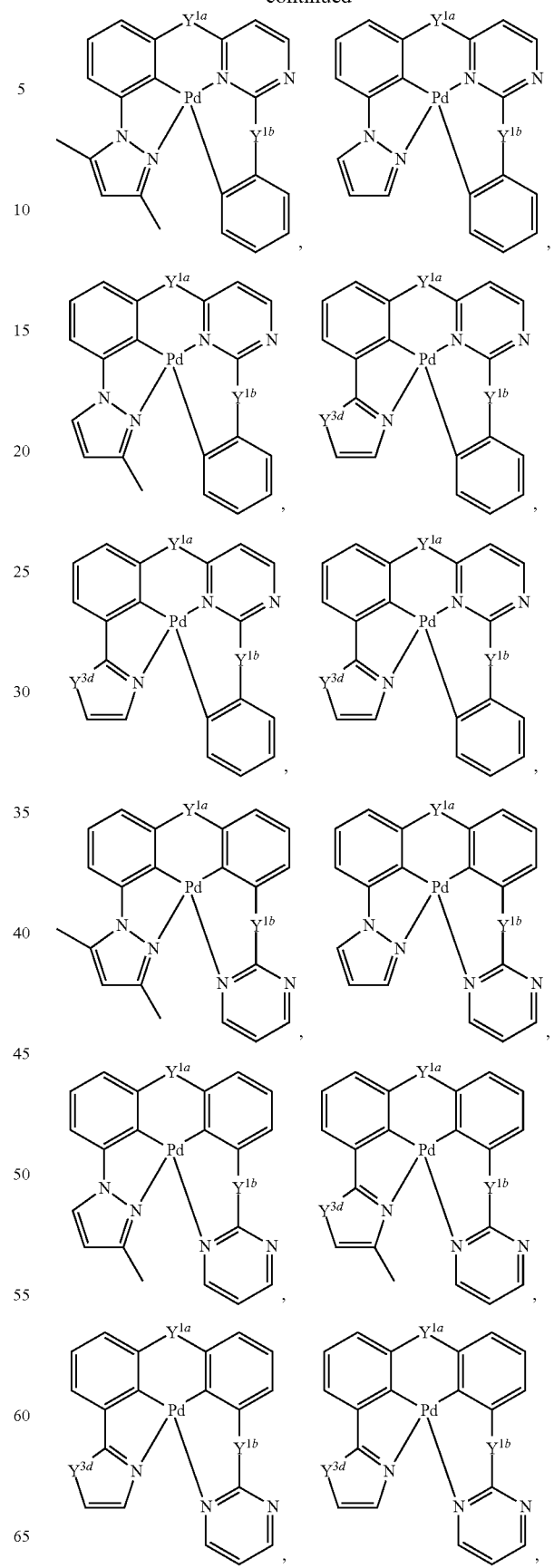

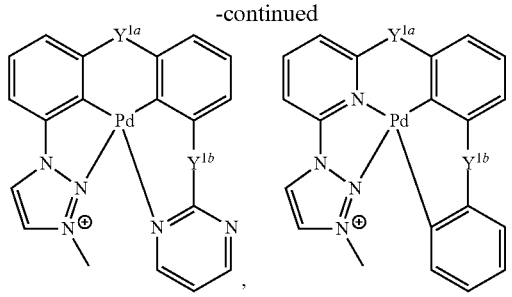
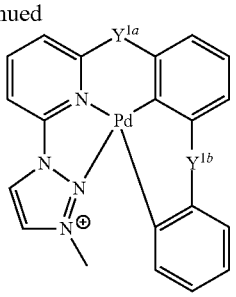
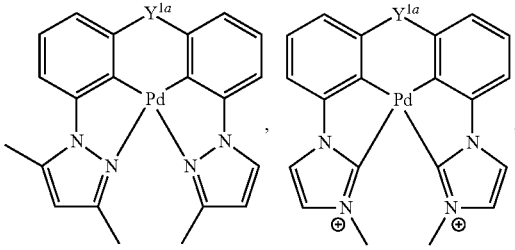
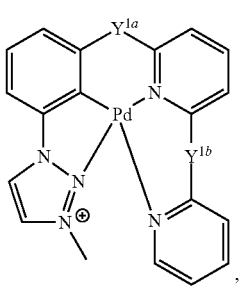
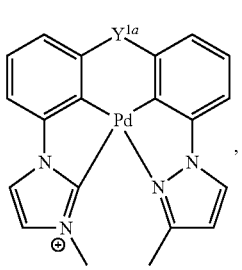
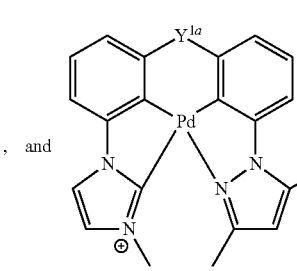
In another embodiment of the general formula above, the compound is represented by the formula:
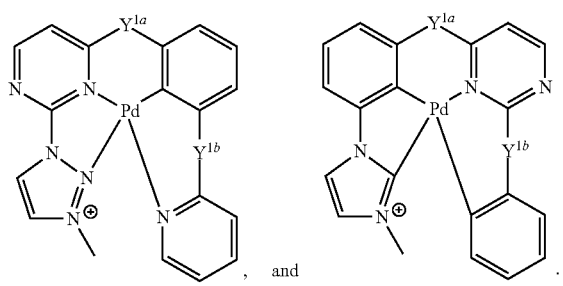
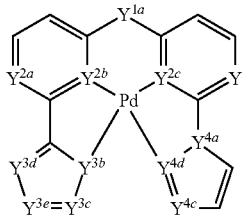, or 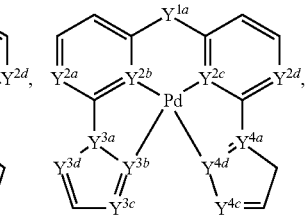
In another embodiment of the general formula above, the compound is represented by the formula:
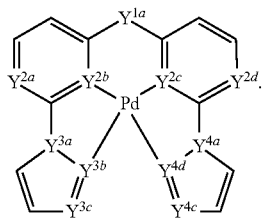
Non-limiting examples of specific embodiments within this formula include:
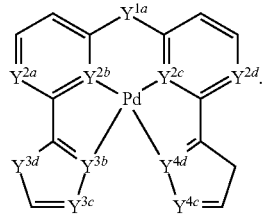
Non-limiting examples of specific embodiments within these formula include:
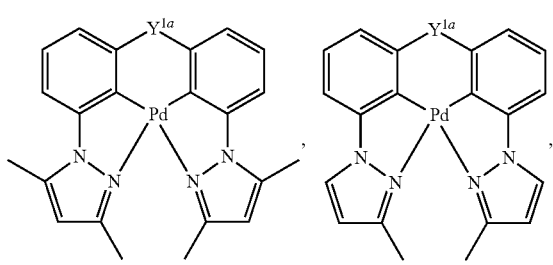
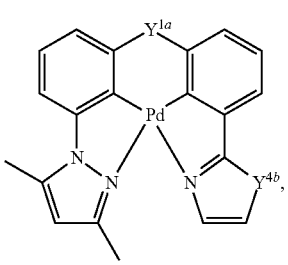

-continued

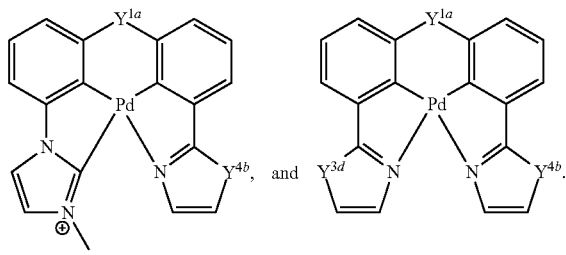

In other aspects, any one or more of the general formulas and/or specific examples recited herein can be excluded from the invention. For example, in one aspect, the formula

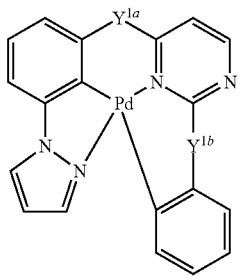

is not included in the present invention.

The compounds of the invention can be made using a variety of methods. In one embodiment, wherein $Y^{1a}$ is O, the compounds can be provided according to Scheme 1.

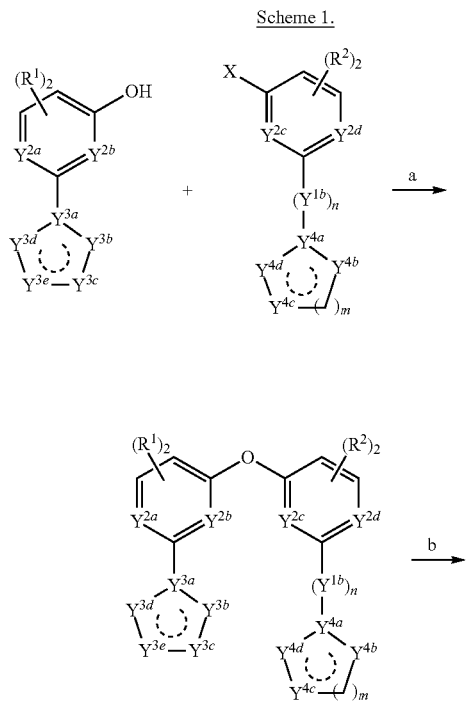

-continued

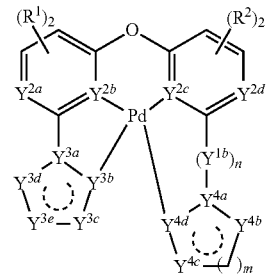

With reference to Scheme 1, step "a" can be accomplished, for example, by using a catalytic amount of a coupling reagent, such as $Cu_2O$, which couples alcohols, particularly phenols, with halogenated phenyl groups. The variable "X" in Scheme 1 above represents a halogen (i.e., Cl, F, I, Br), and is preferably I when used in conjunction with Scheme 1.

Each side of a ligand which complexes a metal can be made independently using a variety of methods, which, in one aspect, depend on whether $Y^{3a}$ is N or C. With reference to Scheme 2 below, when $Y^{4a}$ is N, the precursor can, in one aspect, be provided according to Scheme 2(A), wherein a halogenated phenyl compound is reacted with a pyrazole, imadazole, 1H-1,2,3-triazole, 1H-tetrazole, or 2H-pentazole. In such an aspect, the halogenated phenyl compound can comprise any halogen (X), including Cl, Br, F, or I, but is preferably I, which is typically more reactive in a coupling reaction. The halogenated phenyl compound and corresponding pyrazole, imadazole, 1H-1,2,3-triazole, 1H-tetrazole, or 2H-pentazole can be coupled using a metallic and/or organometallic coupling agent, such as, for example, $Cu_2O$. During such a coupling reaction, it can, in one aspect, be advantageous to include an acid scavenger, such as, for example, syn-2-pyridinealdoxime, in a small molar ratio, for example, about 20 mol %.

In another aspect, when $Y^{4a}$ is C, a different protocol can be used to provide the precursor. With reference to Scheme 2(B) below, a halogenated phenyl, as discussed above can be reacted with a tetrazole, 1,2,3-triazole, pyrazole, or pyrrole to achieve a carbon-carbon bond coupling, as opposed to a carbon-nitrogen bond coupling as shown in Scheme 2(A). In one aspect, the carbon-carbon bond coupling can also be achieved using an organometallic catalyst, such as, for example, a Pd(II) catalyst (e.g., $Pd(OAc)_2$) in a small molar ratio. In one aspect, such an organometallic catalyst can optionally be used together with an excess of a salt mixture, such as KI and/or CuI. As one of skill in the art can appreciate, when employing each of the coupling reactions shown in Scheme 2, it can, in various aspects, be advantageous to perform the reactions in a dry atmosphere, for example under argon, or even in a dry box to minimize and/or avoid moisture or oxygen inclusion.

Scheme 2.

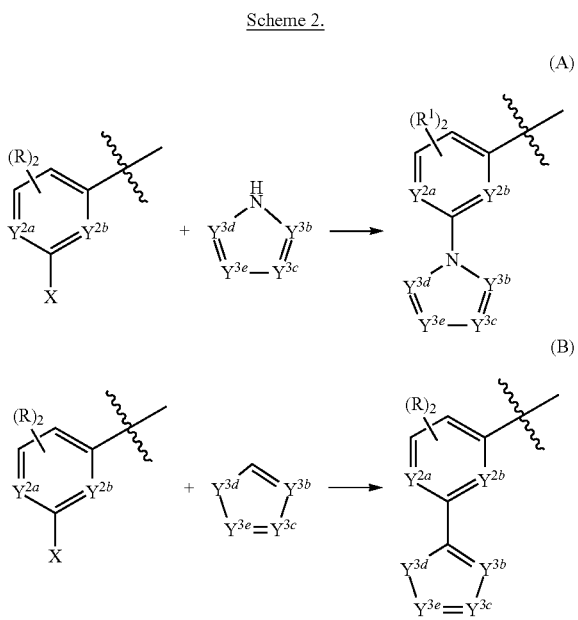

Figure 3:
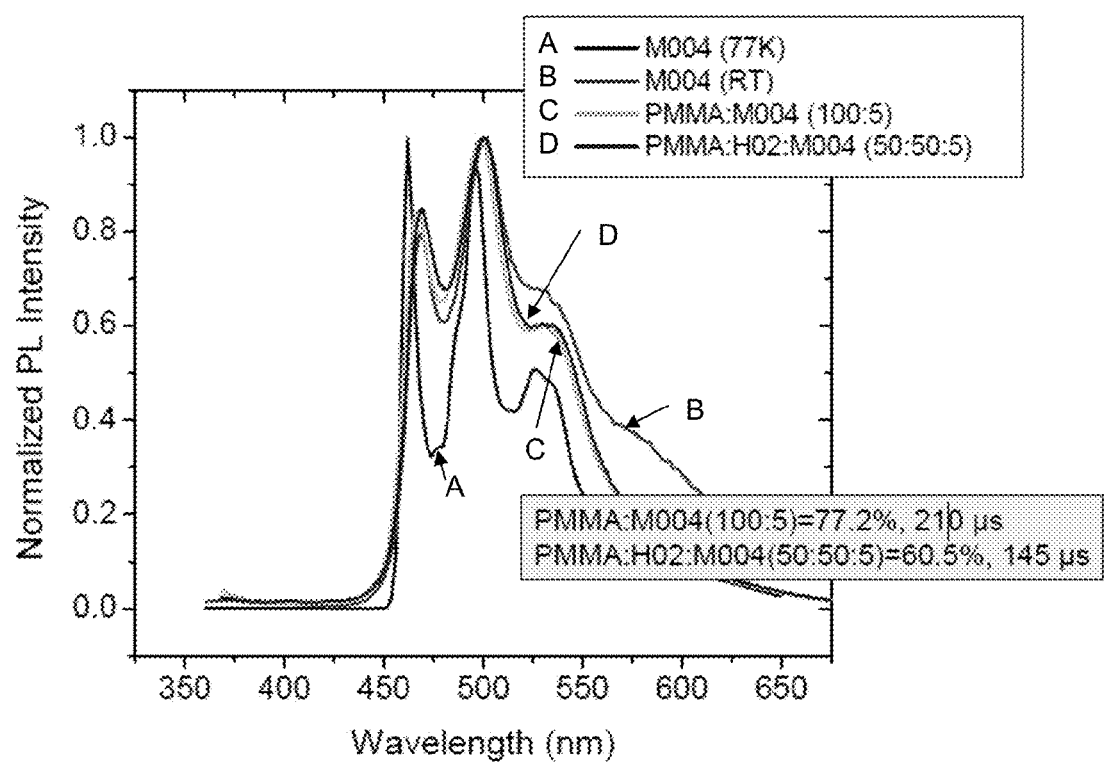
FIG. 3 is a photoluminescence spectrum produced from a specific embodiment, 2-(3-(pyridin-2-yl)phenoxy)-6-(pyridin-2-yloxy)phenyl]Pd(II) (Pd003) doped into a polymethylmethacrylate (PMMA) thin film at room temperature, which shows a thin film photoluminescence quantum yield over 70%.
Figure 4:
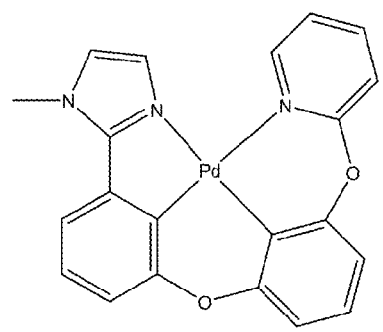
FIG. 4 illustrates (A) a specific embodiment, and (B) a photoluminescence spectrum of the same in a solution of dichloromethane, obtained at room temperature wherein the quantum yield was about 0.16 and the luminescent lifetime was about 30 nsec.
Figure 4:
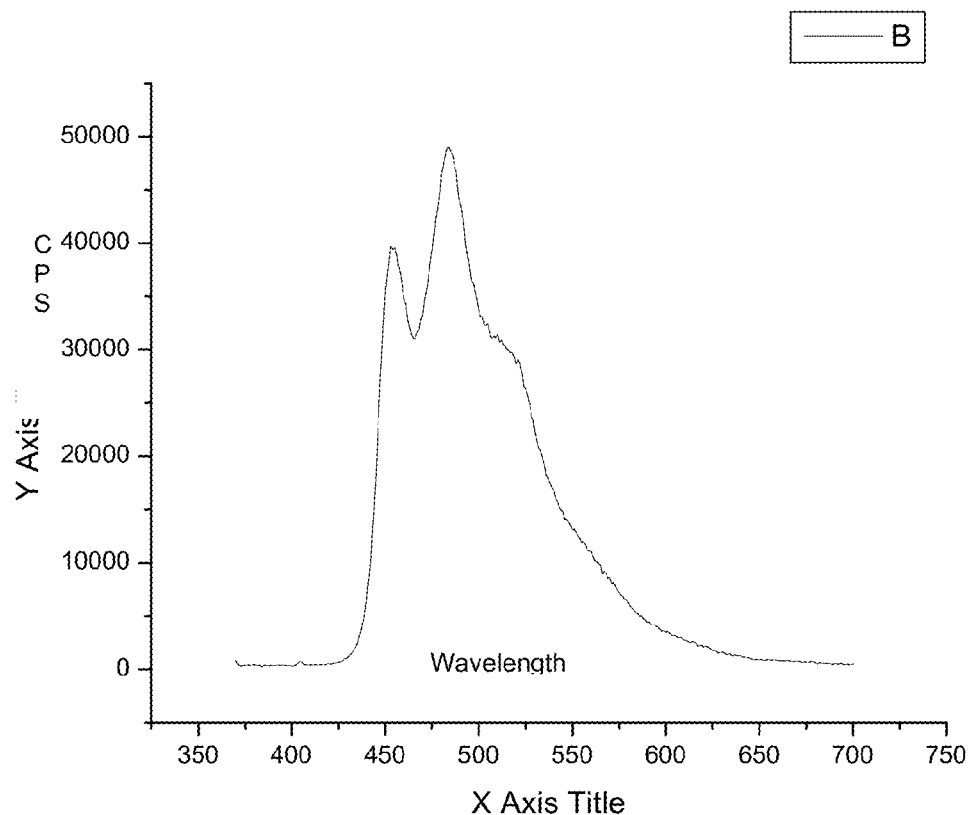
Figure 5:
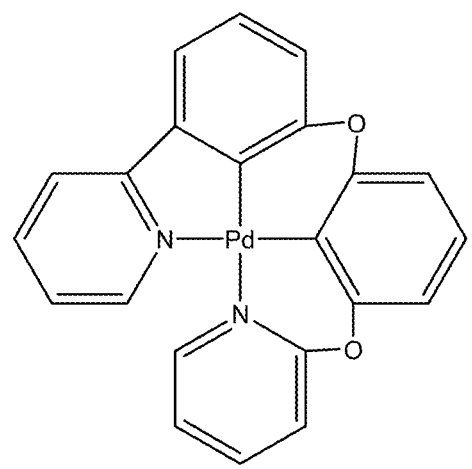
FIG. 5 illustrates (A) a specific embodiment, (B) an electroluminescent spectrum from a OLED device comprising the specific embodiment, (C) a plot of external quantum efficiency vs. current density for a Pd003 based device, and (D) a current vs. voltage plot at a 1% doping level.
Figure 5:
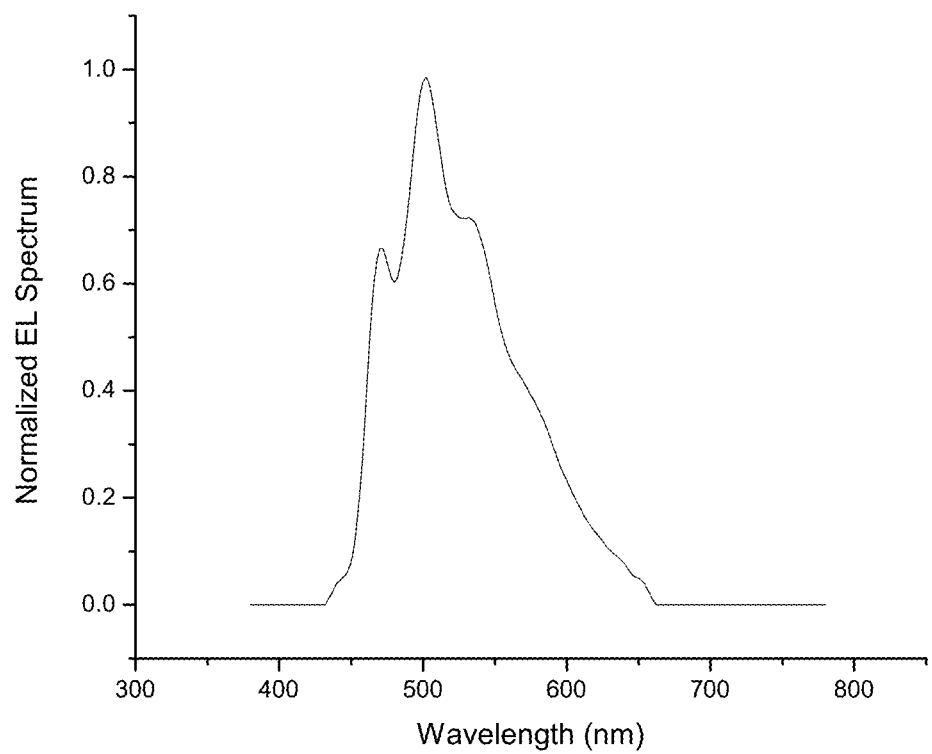
Figure 5:
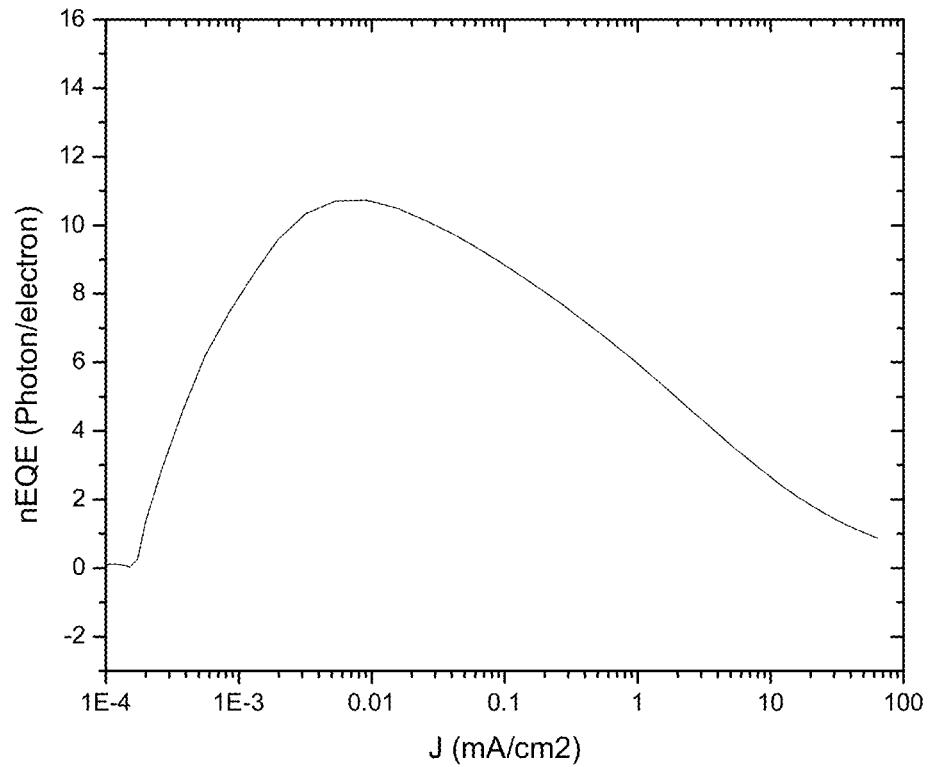
Figure 5:
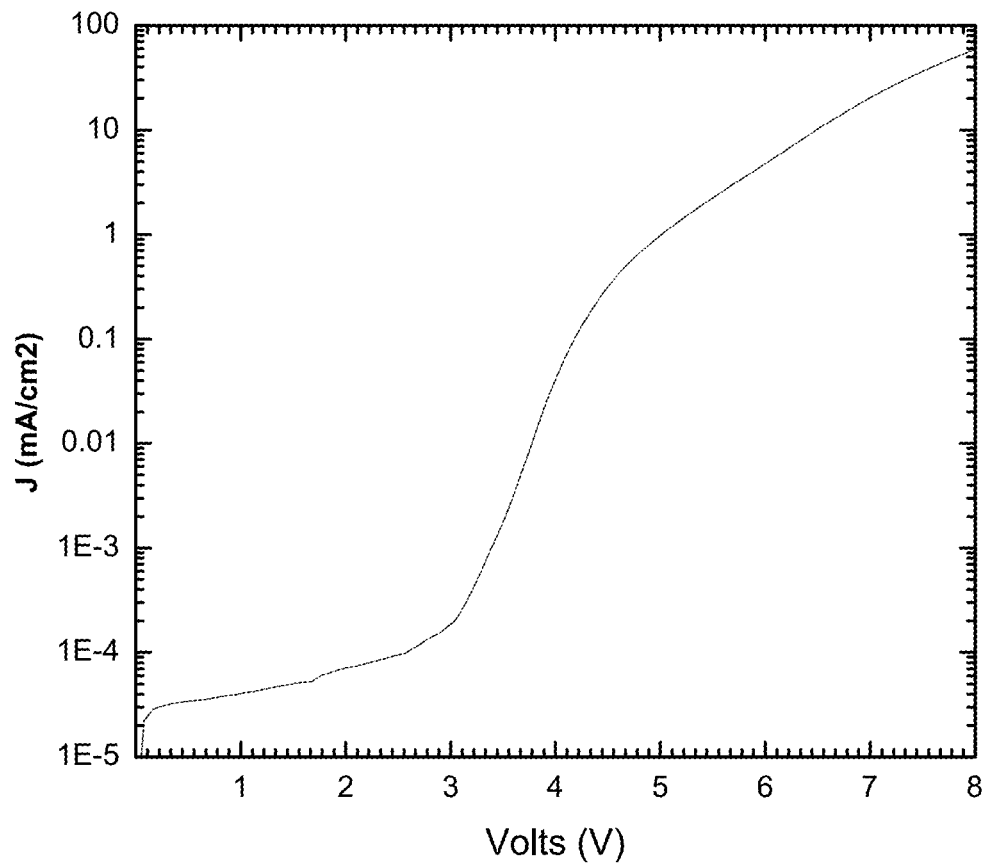

In one aspect, the compounds of the invention can be useful in a variety of optical applications. When utilized as light emitting materials, the inventive compounds can be useful in organic light emitting diodes (OLED)s, luminescent devices and displays, and/or other light emitting devices. With reference to FIG. 3, for example, a specific embodiment, 2-(3-(pyridin-2-yl)phenoxy)-6-(pyridin-2-yloxy)phenyl]Pd(II) exhibits photoluminescence (absorption of light followed by emission of light) across a range of wavelengths, including a narrow blue emission and other emission bands out to the red to near-IR region of the spectrum.

The emission (and absorption) profile of the compounds can be tuned by varying the structure of the ligand surrounding the metal center. For example, compounds having a ligand with electron withdrawing substituents can, in one aspect, generally exhibit different optical properties, including emission and absorption, than compounds having a ligand with electron donating substituents. Generally, a chemical structural change can affect the electronic structure of the compound, thereby affecting the absorption and emission properties of the compound. Thus, the compounds of the present invention can be tailored or tuned to a specific application that desires a particular emission or absorption characteristic. One of skill in the art, in possession of this disclosure, could readily design and/or select an appropriate multidentate palladium compound, in accordance with the various aspects described herein, to use in a particular application.

In one embodiment, the compounds can be used in an OLED. FIG. 1 illustrates a cross-sectional view of an exemplary OLED 100, which includes substrate 102 with an anode 104, which is typically a transparent material, such as indium tin oxide, a layer of hole-transporting material(s) (HTL) 106, a layer of light processing material 108, such as an emissive material (EML) including an emitter and a host, a layer of electron-transporting material(s) (ETL) 110, and a metal cathode layer 112.

In such an embodiment, the layer of light processing material 108 can comprise one or more compounds of the present invention optionally together with a host material. The host material, if present, can be any suitable host material known in the art. The emission color of an OLED can be determined by the emission energy (optical energy gap) of the light processing material 108, which as discussed above can be tuned by tuning the electronic structure of the emitting compounds and/or the host material. Both the hole-transporting material in the HTL layer 106 and the electron-transporting material(s) in the ETL layer 110 can comprise any suitable hole-transporter known in the art. A selection of which is well within the purview of those skilled in the art.

It will be apparent that the compounds of the present invention can exhibit phosphorescence. Phosphorescent OLEDs (i.e., OLEDs with phosphorescent emitters) typically have higher device efficiencies that other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of specific embodiment 2-(3-(pyridin-2-yl)phenoxy)-6-(pyridin-2-yloxy)phenyl]Pd(II)

Synthesis of 3-(pyridin-2-yloxy)phenol

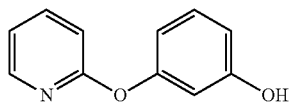 [SMILES: Oc1cccc(Oc2ccccn2)c1]

Under a nitrogen atmosphere, a pressure vessel was charged with a magnetic stir bar, resorcinol (110 mmol), 2-bromopyridine (100 mmol), 1-methylimidazole (5 mmol), and potassium carbonate (200 mmol). Pyridine (80 mL) was added and bubbled with nitrogen for 20 minutes before copper(I) iodide (10 mmol) was added and bubbled 10 minutes further. The vessel was sealed and heated to 140° C. while stirring. After 2 days, the solution was allowed to cool. The solids were filtered off and rinsed with a 50:50 mixture of toluene and methanol. The filtrate was reduced by rotary evaporation and 150 ml of water containing 10 mL glacial acetic acid was added and shaken vigorously. The water was decanted off and 50 mL of DCM was added, forming an off white precipitate which was collected by vacuum filtration and dried with ether, resulting in the pure product 3-(pyridin-2-yloxy)phenol with a 55% yield. $^1$H NMR (CDCl$_3$): 5.98 (s, 1H), 6.59 (s, 1H), 6.62-6.69 (m, 2H), 6.94 (d, 1H), f 7.02 (dd, 1H), 7.23 (vt, 1H), 7.70 (dd, 1H), 8.23 (b, 1H)

Synthesis of 2-(3-(3-bromophenoxy)phenoxy)pyridine

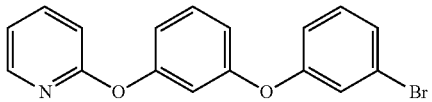 [SMILES: Brc1cccc(Oc2cccc(Oc3ccccn3)c2)c1]

Under a nitrogen atmosphere, a pressure vessel was charged with a magnetic stir bar, 3-(pyridin-2-yloxy)phenol (50 mmol), 2,6-dibromopyridine (50 mmol), 1-methylimidazole (25 mmol), and potassium carbonate (100 mmol). Toluene (80 mL) was added and bubbled with nitrogen for 20 minutes before copper(I) iodide (5 mmol) was added and the solution bubbled for 10 minutes further. The vessel was sealed and heated to 140° C. while stirring. After 2 days, the solution was allowed to cool and the solids were filtered off and rinsed with dichloromethane. The filtrate was added to a separatory funnel containing DCM and water. The water phase was washed 3 times with 75 mL DCM, and the combined organic layers were washed once with pure water. The organic layer was collected, dried with magnesium sulfate, filtered, and the filtrate reduced by rotary evaporation. The resulting oil was purified by column chromatography using DCM over silica resulting in the pure product 2-(3-(3-bromophenoxy)phenoxy)pyridine with a 60% yield. $^1$H NMR (CDCl$_3$): 6.80-6.85 (m, 2H), 6.91 (s, 1H), 6.94 (s, 1H), 6.97-7.03 (m, 2H), 7.19 (vt, 1H), 7.21-7.24 (m, 2H), 7.36 (vt, 1H), 7.70 (dd, 1H), 8.21 (dd, 1H).

Synthesis of 2-(3-(3-(pyridin-2-yl)phenoxy)phenoxy)pyridine

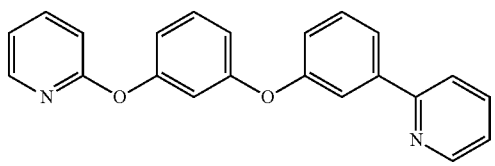 [SMILES: c1ccc(Oc2cccc(Oc3cccc(-c4ccccn4)c3)c2)nc1]

Under a nitrogen atmosphere, an oven dried three neck flask was charged with a magnetic stir bar, 2-(3-(3-bromophenoxy)phenoxy) (10 mmol), and 2-(tripropylstannyl)pyridine (10 mmol). Dry toluene (100 mL) was added and bubbled with nitrogen for 20 minutes before Tetrakis(triphenylphosphine)palladium(0) (0.5 mmol) was added, bubbled 10 minutes further, and brought to reflux for 2 days. After cooling, the contents of the flask were filtered, the liquid reduced by rotary evaporation, and the resulting oil was purified by column chromatography using DCM over silica to yield the pure product 2-(3-(3-(pyridin-2-yl)phenoxy)phenoxy)pyridine with a 65% yield. $^1$H NMR (CDCl$_3$): 6.84 (vt, 1H), 6.85-6.89 (m, 2H), 6.91 (d, 1H), 6.98 (dd, 1H), 7.11 (dd, 1H), 7.24 (dd, 1H), 7.34 (vt, 1H), 7.44 (vt, 1H), 7.66-7.78 (m, 5H), 8.19 (dd, 1H), 8.67 (dd, 1H).

Synthesis of [2-(3-(pyridin-2-yl)phenoxy)-6-(pyridin-2-yloxy)phenyl]Pd(II)

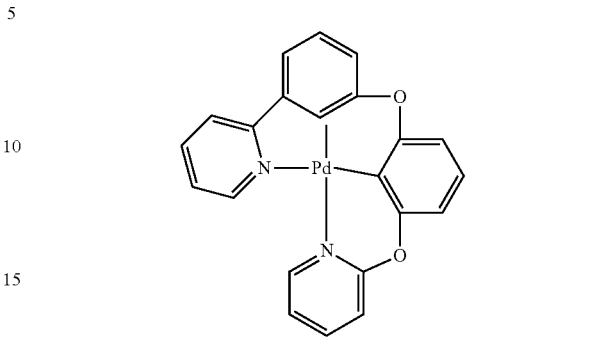

A mixture of 2-(3-(3-(pyridin-2-yl)phenoxy)phenoxy)pyridine (1 mmol), K$_2$PdCl$_4$ (1 mmol), and acetic acid (10 mL) was refluxed for 3 days. The mixture was allowed to cool to room temperature. The resulting white complex was filtered off and washed with H$_2$O, MeOH, and Et$_2$O, and dried under vacuum to 2-(3-(pyridin-2-yl)phenoxy)-6-(pyridin-2-yloxy)phenyl]Pd(II). The product was purified by sublimation for further testing.

What is claimed is:

1. A compound represented by one of the following formulas:

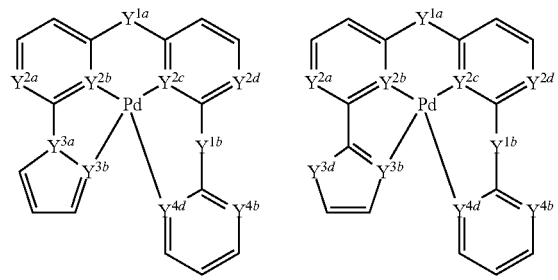

wherein:

$Y^{1a}$ represents O, S, NR$^{4a}$, wherein R$^{4a}$ represents optionally substituted C$_1$-C$_4$ alkyl; or C(R$^{4c}$)$_2$, wherein each R$^{4c}$ in (R$^{4c}$)$_2$ represents hydrogen or optionally substituted C$_1$-C$_4$ alkyl;

$Y^{1b}$ represents O, S, NR$^{5a}$, wherein R$^{5a}$ represents optionally substituted C$_1$-C$_4$ alkyl; or C(R$^{5c}$)$_2$, wherein each R$^{5c}$ in (R$^{5c}$)$_2$ represents hydrogen or optionally substituted C$_1$-C$_4$ alkyl;

each of $Y^{2a}$, $Y^{2b}$, $Y^{2c}$, and $Y^{2d}$ independently represents N, NR$^{6a}$, or CR$^{6b}$, wherein each of R$^{6a}$ and R$^{6b}$ is independently absent or independently represents hydrogen or optionally substituted C$_1$-C$_4$ alkyl; and each of $Y^{3a}$, $Y^{3b}$, $Y^{3d}$, $Y^{4b}$, and $Y^{4d}$ independently represents N, O, S, NR$^{6a}$, CR$^{6b}$, wherein each of R$^{6a}$ and R$^{6b}$ is independently absent or independently represents hydrogen or optionally substituted C$_1$-C$_4$ alkyl.

2. An organic light-emitting diode (OLED) comprising, as an emissive material, the compound of claim 1.

3. An organic photovoltaic device comprising, as a donor or acceptor material, the compound of claim 1.
4. A compound of represented by one of the following formulas:
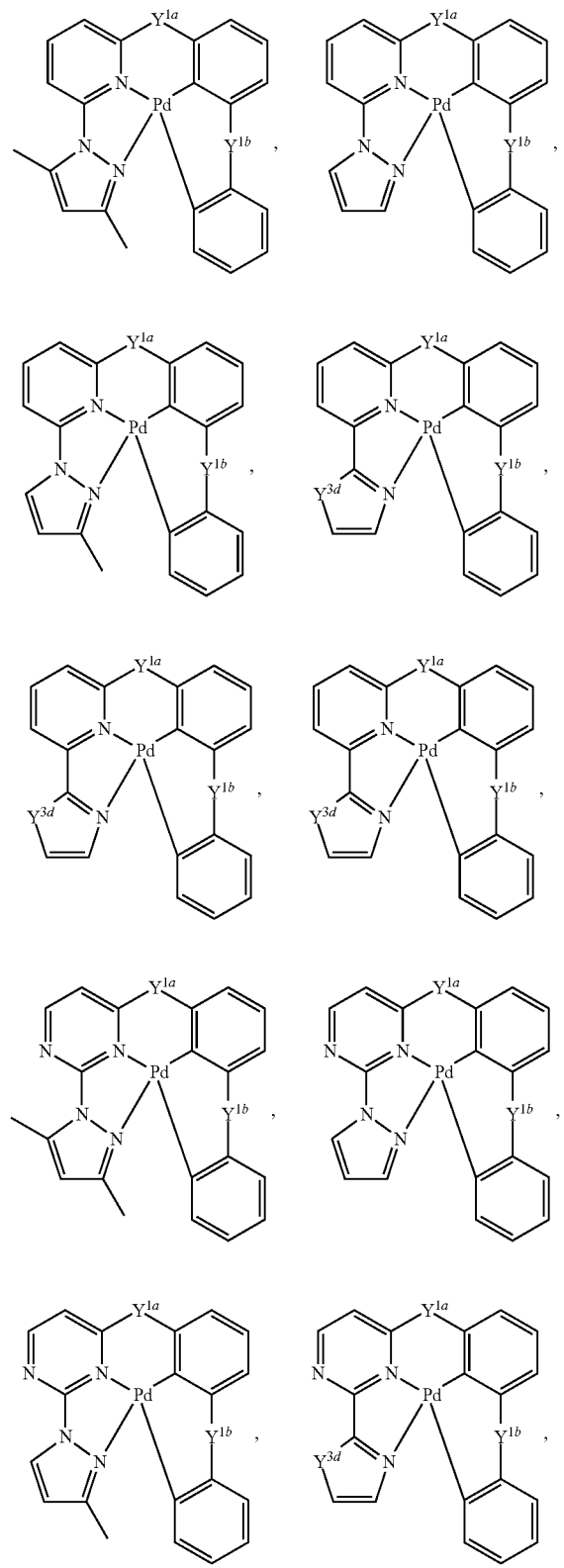
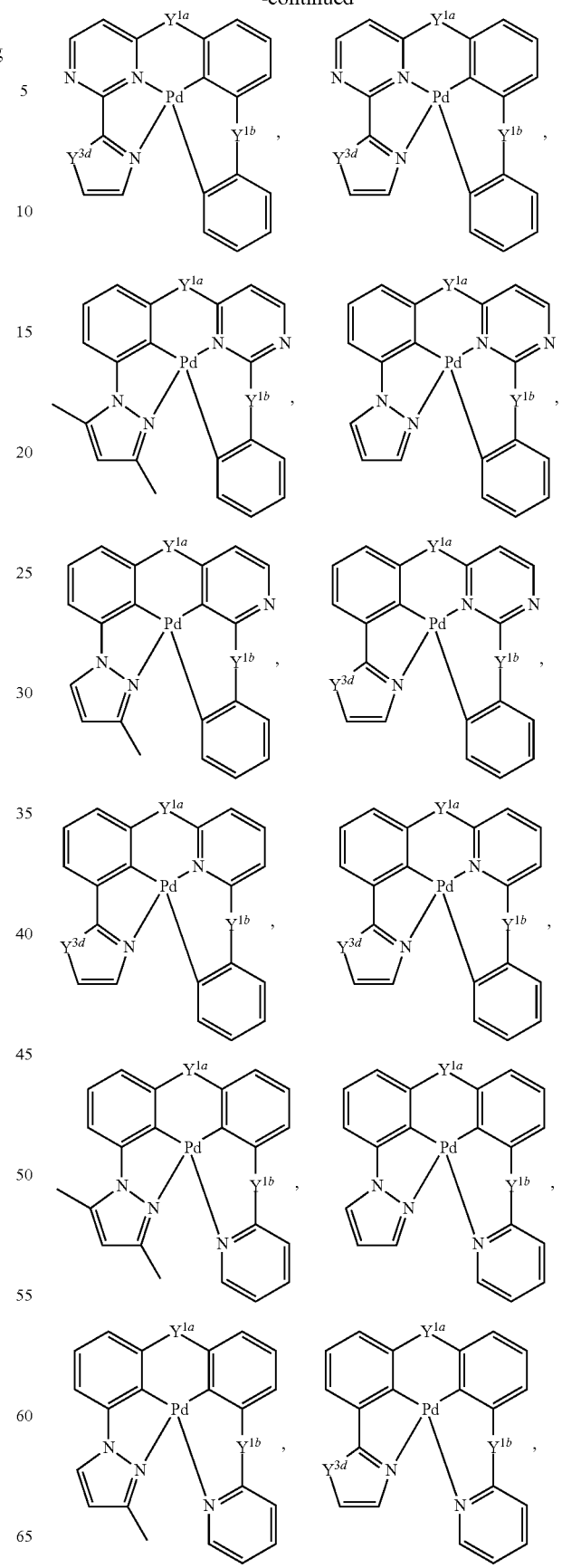

-continued

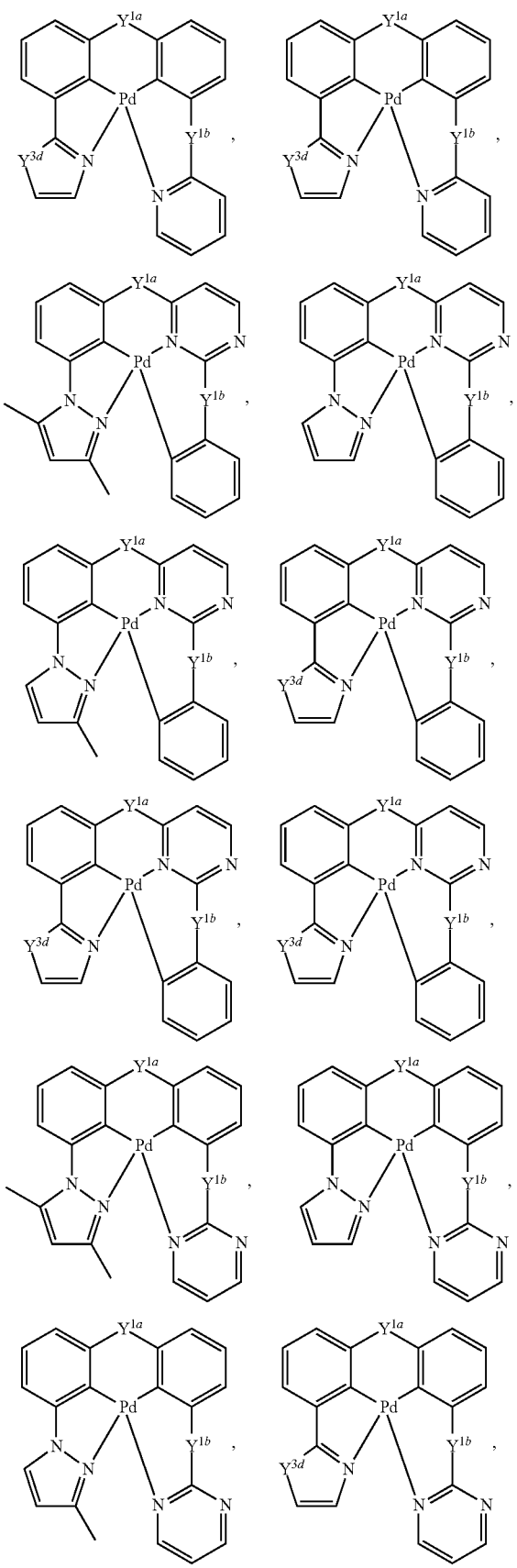

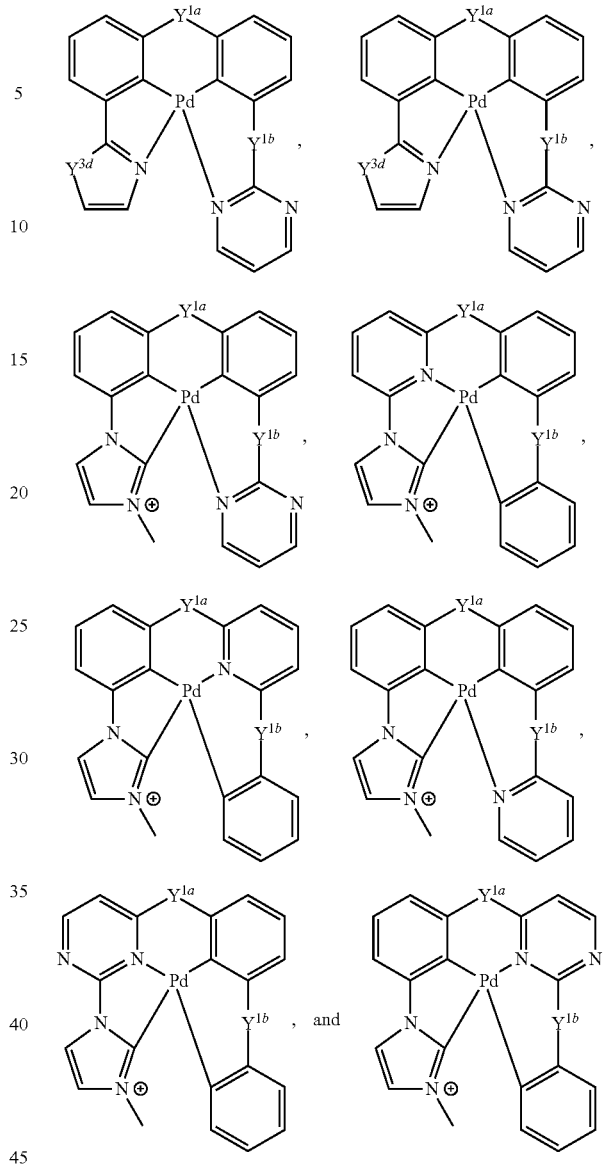

wherein:
Y$^{1a}$ represents O, S, NR$^{4a}$, wherein R$^{4a}$ represents optionally substituted C$_1$-C$_4$ alkyl; or C(R$^{4c}$)$_2$, wherein each R$^{4c}$ in (R$^{4c}$)$_2$ represents hydrogen or optionally substituted C$_1$-C$_4$ alkyl;

Y$^{1b}$ represents O, S, NR$^{5a}$, wherein R$^{5a}$ represents optionally substituted C$_1$-C$_4$ alkyl; or C(R$^{5c}$)$_2$, wherein each R$^{5c}$ in (R$^{5c}$)$_2$ represents hydrogen or optionally substituted C$_1$-C$_4$ alkyl; and Y$^{3d}$ represents N, O, S, NR$^{6a}$, CR$^{6b}$, wherein each of R$^{6a}$ and R$^{6b}$ is independently absent or independently represents hydrogen or optionally substituted C$_1$-C$_4$ alkyl.

5. An organic light-emitting diode (OLED) comprising, as an emissive material the compound of claim 4.

6. An organic photovoltaic device comprising, as a donor or acceptor material, the compound of claim 4.

7. A compound represented by one of the following formulas:

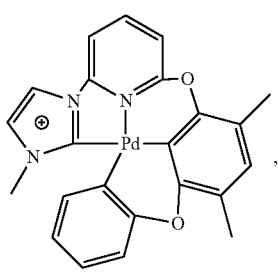
,

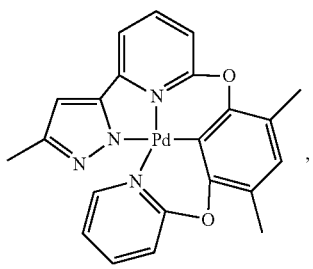
,

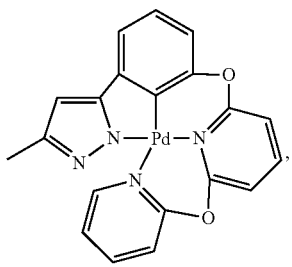
,

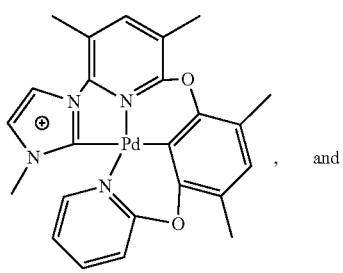
, and

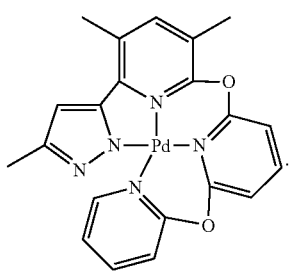
.

8. An organic light-emitting diode (OLED) comprising, as an emissive material, the compound of claim 7.

9. An organic photovoltaic device comprising, as a donor or acceptor material, the compound of claim 7.

10. A compound represented by the formula:

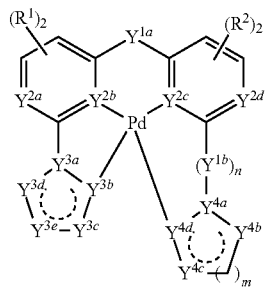

wherein:
each $R^1$ and $R^2$ in $(R^1)_2$ and $(R^2)_2$ independently represents hydrogen;
$Y^{1a}$ represents O, S, or $NR^{4a}$, wherein $R^{4a}$ represents optionally substituted $C_1$-$C_4$ alkyl;
n is an integer 1;
$Y^{1b}$ represents O, S, or $NR^{5a}$, wherein $R^{5a}$ represents optionally substituted $C_1$-$C_4$ alkyl;
each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, or optionally substituted $C_1$-$C_4$ alkyl;
each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$ or $CR^{6b}$, wherein each of $R^{6a}$ and $R^{6b}$ independently represents hydrogen or optionally substituted $C_1$-$C_4$ alkyl;
wherein m is an integer 1 or 2;
wherein the open dotted circle indicates partial or full unsaturation of the ring with which it is associated;
provided that if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$, or $Y^{3d}$ is not N.

11. The compound of claim 10, which is represented by the formula:

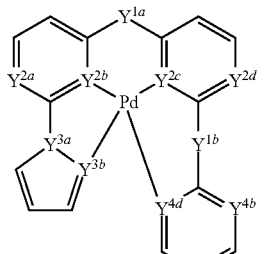
or

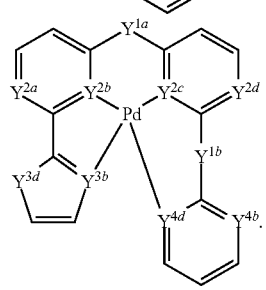
.

12. An organic light-emitting diode (OLED) comprising, as an emissive material, a compound represented by the formula of claim 10.

13. An organic photovoltaic device comprising, as a donor or acceptor material, a compound represented by the formula of claim 10.

* * * * *